United States Patent
Wang et al.

(10) Patent No.: US 11,135,187 B2
(45) Date of Patent: Oct. 5, 2021

(54) COMPOSITIONS AND METHODS FOR TREATING DIABETIC RETINOPATHY

(71) Applicant: Augusta University Research Institute, Inc., Augusta, GA (US)

(72) Inventors: Mong Heng Wang, Martinez, GA (US); Mohamed Al-Shabrawey, Evans, GA (US)

(73) Assignees: National Institutes of Health (NIH), Bethesda, MD (US); U.S. Dept. of Health Human Services, (DHHS), Bethesda, MD (US); U.S. Government NIH Division of Extramural Inventions and Technology Resources (DEITR), Bethesda, MD (US)

( * ) Notice: Subject to any disclaimer, the term of this patent is extended or adjusted under 35 U.S.C. 154(b) by 0 days.

(21) Appl. No.: 16/106,421

(22) Filed: Aug. 21, 2018

(65) Prior Publication Data

US 2019/0060259 A1    Feb. 28, 2019

Related U.S. Application Data

(60) Provisional application No. 62/548,487, filed on Aug. 22, 2017.

(51) Int. Cl.
| | | |
|---|---|---|
| *A61K 31/18* | (2006.01) | |
| *A61P 25/00* | (2006.01) | |
| *A61K 31/336* | (2006.01) | |
| *A61P 27/02* | (2006.01) | |
| *A61K 31/4184* | (2006.01) | |
| *A61K 9/00* | (2006.01) | |
| *A61K 31/4178* | (2006.01) | |

(52) U.S. Cl.
CPC ............ *A61K 31/18* (2013.01); *A61K 9/0019* (2013.01); *A61K 9/0048* (2013.01); *A61K 9/0053* (2013.01); *A61K 31/336* (2013.01); *A61K 31/4178* (2013.01); *A61K 31/4184* (2013.01); *A61P 25/00* (2018.01); *A61P 27/02* (2018.01)

(58) Field of Classification Search
CPC .. A61K 31/18; A61K 31/336; A61K 31/4178; A61K 31/4184; A61K 9/0019; A61K 9/0048; A61K 9/0053; A61P 25/00; A61P 27/02

See application file for complete search history.

(56) References Cited

U.S. PATENT DOCUMENTS

| 5,013,556 A | 5/1991 | Woodle | |
|---|---|---|---|
| 2005/0038093 A1* | 2/2005 | Yamagishi | G01N 33/74 |
| | | | 514/381 |

FOREIGN PATENT DOCUMENTS

JP    2003238441    *    8/2003

OTHER PUBLICATIONS

Khardori, Medscape, Apr. 2020, https://emedicine.medscape.com/article/117739-clinical#b3 (Year: 2020).*
(Whitehead et al, Expert Opinion on Biological Therapy, 2018, vol. 18, No. 12, 1257-1270). (Year: 2018).*
Hideyuki et al. (JP 2003238441, English translation ) (Year: 2003).*
Nithipatikom et al. (Cancer Sci, Dec. 2010, 101, 12, 2629-36). (Year: 2010).*
Gong et al. (The Am J of Clinical Nutrition, 106, Jul. 2017, p. 16-26) (Year: 2017).*
Abuchowski, Abraham, et al., "Soluble Polymer-Enzyme Adducts", Enzymes as Drugs, pp. 367-383 (1981).
Chaturvedi, Nish, et al., "Effect of Candesartan on Prevention (DIRECT-Prevent1) and Progression (DIRECT-Protect1) of Retinopathy in Type 1 Diabetes: Randomised, Placebo-Controlled Trials" The Lancet, 372:1394-1402 (2008).
Fouda, Abdelrahman Y., et al., "Renin-Angiotensin System as a Potential Therapeutic Target in Stroke and Retinopathy: Experimental and Clinical Evidence", Clin Sci (Lond), 130:221-238 (2016).
Huang, Hui, et al., "Epoxyeicosatrienoic Acid Inhibition Alters Renal Hemodynamics During Pregnancy", Exp Biol Med (Maywood), 231:1744-1752 (2006).
Liu, Jun-Yan, et al., "Pharmacokinetic Optimization of Four Soluble Epoxide Hydrolase Inhibitors for Use in a Murine Model of Inflammation", Br J Pharmacol, 156:284-296 (2009).
Lorthioir, Aurelien, et al., "Diabetic CVD—Soluble Epoxide Hydrolase as a Target", Cardiovasc Hematol Agents Med Chem, 10:212-222 (2012).
Marshall, Keith, "Solid Oral Dosage Forms", Modem Pharmaceutics, pp. 359-427 (1979).
Mathiowitz, E., et al., "Novel Microcapsules for Delivery Systems", Reactive Polymers, 6:275-283 (1987).
Mathiowitz, E., et al., "Polyanhydride Microspheres as Drug Carriers I. Hot Melt Microencapsulation", J Controlled Release, 5:13-22 (1987).
Mathiowitz, E., et al., "Polyanhydride Microspheres as Drug Carriers. II. Microencapsulation by Solvent Removal", J Appl Polymer Sci, 35:755-774 (1988).

(Continued)

*Primary Examiner* — Umamaheswari Ramachandran
(74) *Attorney, Agent, or Firm* — Smith Gambrell & Russell

(57) ABSTRACT

Compositions and methods for treating diabetic retinopathy or symptoms thereof are provided. The disclosed compositions and methods for treating diabetic retinopathy contravene the existing paradigm that Renin-Angiotensin System (RAS) blockade alone can treat, prevent, or reduce diabetic retinopathy. The disclosed compositions and methods include a combination or alternation of EET antagonists and ATI antagonists.

3 Claims, 20 Drawing Sheets

(56) References Cited

OTHER PUBLICATIONS

Newmark, J., et al., "Preparation and Properties of Adducts of Streptokinase and Streptokinase-Plasmin Complex with Polyethylene Glycol and Pluronic Polyol F38", J Appl Biochem, 4:185-189 (1982).

* cited by examiner

COMPOSITIONS AND METHODS FOR TREATING DIABETIC RETINOPATHY

CROSS-REFERENCE TO RELATED APPLICATIONS

This application claims benefit of and priority to U.S. Provisional Patent Application No. 62/548,487 filed on Aug. 22, 2017, which is incorporated by reference in its entirety.

STATEMENT REGARDING FEDERALLY SPONSORED RESEARCH

This invention was made with government support under EY023315 awarded by the National Institutes of Health. The government has certain rights in the invention.

FIELD OF THE INVENTION

The invention is generally directed to compositions and methods for treating diabetic retinopathy.

BACKGROUND OF THE INVENTION

Diabetic retinopathy (DR), a common microvascular complication of diabetes and the leading cause of blindness, affects nearly 7.7 million working-age adults in the U.S. Diabetes-related blindness costs approximately S500 million annually in the U.S. Loss of blood-retinal barrier (BRB) function, a key stage in the pathogenesis of DR, leads to diabetic macular edema (DME) and subsequently loss of vision. Although advances, including tight glycemic control, laser photocoagulation, anti-vascular endothelial growth fact (VEGF), and corticosteroid therapy, have been made in treating DR, these methods are limited by significant side effects and do not completely eliminate the risk of blindness.

The renin-angiotensin system (RAS) in the retina is activated in DR. RAS activation contributes to retinal hyperpermeability and retinal neovascularization in DR. Although the blockade of RAS with an AT1 receptor blocker has reduced the incidence of DR in clinical studies, AT1 blockade did not reduce the progression of DR in diabetic patients. Thus, the US Food and Drug Administration (FDA) still does not approve the use of RAS blockade to treat DR. In short, lack of understanding of the molecular mechanism of retinal microvascular dysfunction induced by RAS is a critical barrier to the use of RAS blockade to prevent or treat DR.

Thus, there is a critical need to identify new therapeutic targets to treat or at least minimize the microvascular dysfunction associated with DR.

It is an object of the invention to provide compositions and methods for treating diabetic retinopathy.

It is another object of the invention to provide compositions and methods for treating one or more symptoms of diabetic retinopathy.

It is still another object of the invention to provide compositions and methods for inhibit or delaying the onset of diabetic retinopathy.

It is yet another object of the invention to provide compositions and methods for inhibiting or reducing the progression of diabetic retinopathy.

SUMMARY OF THE INVENTION

Compositions and methods for treating diabetic retinopathy or symptoms thereof are provided. The disclosed compositions and methods for treating diabetic retinopathy contravene the existing paradigm that Renin-Angiotensin System (RAS) blockade alone can treat, prevent, or reduce diabetic retinopathy because the disclosed compositions and methods include a combination or alternation of epoxyeicosatrienoic acid (EET) antagonists and AT1 antagonists.

One embodiment provides a pharmaceutical composition having a) an EET antagonist, and an AT1 receptor antagonist. Exemplary EET antagonists include, but are not limited to N-methylsulfonyl-6-(2-propargyloxyphenyl)hexanamide [MS-PPOH]; 14,15-epoxyeicosa-5(Z)-enoic acid [14,15-EEZE]; 14,15-epoxyeicosa-5(Z)-enoic acid 2-[2-(3-hydroxy-propoxy)-ethoxy]-ethyl ester [14,15-EEZE-PEG]; 14,15-epoxyeicosa-5(Z)-enoic-methylsulfonylimide [14,15-EEZE-mSI]; and combinations thereof. Exemplary AT1 antagonists include, but are limited to losartan, candesartan, eprosartan, irbesartan, olmesartan, telmisartan, valsartan, and combinations thereof.

The EET antagonist and the AT1 antagonist are typically in an amount effective to inhibit or reduce one or more symptoms of diabetic retinopathy or the progression of diabetic retinopathy when administered to a subject in need thereof.

The pharmaceutical compositions optionally include a pharmaceutically acceptable excipient, carrier, or diluent. The compositions can be formulated for enteral or parenteral administration. In one embodiment, the compositions are formulated for intravitreal administration. In still another embodiment, the compositions are ophthalmic formulations for administration into the eye.

One embodiment provides a pharmaceutical composition including a combinations of N-methylsulfonyl-6-(2-propargyloxyphenyl)hexanamide and telmisartan.

Methods for treating diabetic retinopathy or one or more symptoms thereof are also provided. One embodiment provides a method for treating diabetic retinopathy by administering one or more of the disclosed pharmaceutical compositions to a subject in need thereof to treat diabetic retinopathy.

Another embodiment provides a method for inhibiting or reducing progression of diabetic retinopathy in a subject in need thereof by administering one or more of the disclosed pharmaceutical compositions to the subject to inhibit or reduce progression of diabetic retinopathy in the subject.

In some methods, the pharmaceutical composition is administered intravitreally.

DETAILED DESCRIPTION OF THE INVENTION

I. Definitions

Figure 1A:
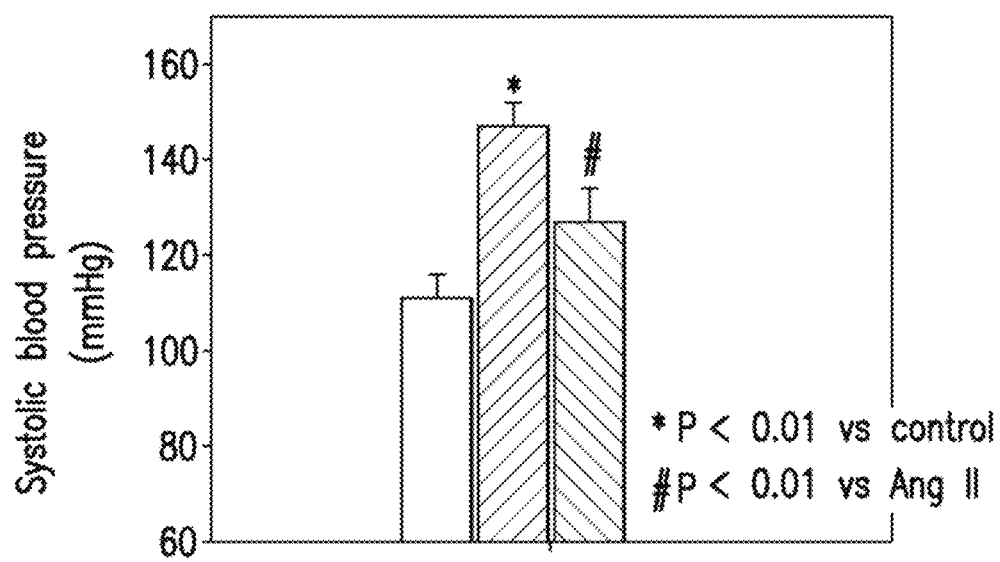
FIG. 1A is a bar graph of systolic blood pressure (mmHg) for control mice (clear rectangle), mice treated with Ang II (black rectangle), or mice treated with Ang II and trans-4-[4-(3-adamantan-1-ylureido)-cyclohexyloxyl]-benzoic acid (t-AUCB). *P<0.01 vs control. #P<0.01 vs Ang II.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "individual," "host," "subject," and "patient" are used interchangeably herein, and refer to a mammal, including, but not limited to, humans, rodents, such as mice and rats, and other laboratory animals.

As used herein, the term "pharmaceutically acceptable carrier or excipient" encompasses any of the standard pharmaceutical carriers, such as a phosphate buffered saline solution, water and emulsions such as an oil/water or water/oil emulsion, and various types of wetting agents.

The term "EETs" refers to epoxyeicosatrienoic acids.

II. Compositions

Compositions for treating diabetic retinopathy are provided. The disclosed compositions and methods of their use contravene the existing paradigm that Renin-Angiotensin System (RAS) blockade alone can prevent or reduce the progression of diabetic retinopathy because the compositions and methods include a combination or alternation of EET antagonists and AT1 antagonists.

In some embodiments, the compositions can be used to treat or inhibit one or more symptoms of diabetic retinopathy. Symptoms of diabetic retinopathy, include but are not limited to spots or dark strings floating in the field of vision, blurred vision, fluctuating vision, impaired color vision, dark or empty areas in the field of vision. In one embodiment, the disclosed compositions can be used to improve patient visual acuity by administering an effective amount of the composition intravitreally to a subject in need thereof.

A. Renin-Angiotensin System (RAS)

In the RAS, prorenin is activated to form renin which converts angiotensinogen to Ang I. Ang I is then hydrolyzed by angiotensin-converting enzyme (ACE) to produce Ang II. Growing evidence demonstrates that RAS is present in the eye, and that activation of RAS is a major factor in the development of diabetic retinopathy. Thus, several clinical studies have focused on determining the effects of RAS blockade in the development of diabetic retinopathy. In the EUCLID trial (530 participants), after two years of treatment, Lisinopril, an ACE inhibitor, reduced the progression of DR by 50% and progression to proliferative DR by 80% (Chaturvedi, N., et al., Effect of lisinopril on progression of retinopathy in normotensive people with type 1 diabetes. The EUCLID Study Group. EURODIAB Controlled Trial of Lisinopril in Insulin-Dependent Diabetes Mellitus. Lancet, 351:28-31 (1998)).

These positive results led to implementation of the DIRECT trial, the largest clinical trial in retinopathy (Chaturvedi, N., et al., Effect of candesartan on prevention (DIRECT-Prevent 1) and progression (DIRECT-Protect 1) of retinopathy in type 1 diabetes: randomized, placebo-controlled trials. Lancet.;372:1394-1402 (2008); Fouda, A. Y., et al., Renin-angiotensin system as a potential therapeutic target in stroke and retinopathy: experimental and clinical evidence. Clin Sci (Lond)., 130:221-38 (2016)). Participants were divided into two groups: the DIRECT-Prevent group (>1,400 participants), which tested whether AT1 blockade can prevent the onset of diabetic retinopathy and the DIRECT-Protect group (>1,900 participants), which tested whether AT1 blockade can reduce the progression of diabetic retinopathy. Although oral treatment with candesartan, an AT1 blocker, decreased the incidence of diabetic retinopathy, AT1 blockade did not reduce the progression of established diabetic retinopathy. Because of these disappointing results, the FDA still does not approve the use of RAS blockade to treat diabetic retinopathy.

B. EETs Blockade

The disclosed compositions include one or more EET antagonists. Exemplary EET antagonists include, but are not limited to N-methylsulfonyl-6-(2-propargyloxyphenyl) hexanamide [MS-PPOH]; 14,15-epoxyeicosa-5(Z)-enoic acid [14,15-EEZE]; 14,15-epoxyeicosa-5(Z)-enoic acid 2-[2-(3-hydroxy-propoxy)-ethoxy]-ethyl ester [14,15-EEZE-PEG]; 14,15-epoxyeicosa-5(Z)-enoic-methylsulfonylimide [14,15-EEZE-mSI], and combinations thereof.

C. AT1 Inhibitors/Antagonists

The disclosed compositions include one or more ATI antagonists. Exemplary AT1 antagonists include, but are not limited to Losartan (Cozaar®), Candesartan (cilexetil or Atacand®); Eprosartan (Teveten®); Irbesartan (Aprovel®); Olmesartan (medoxomil or Olmetec®); Telmisartan (Micardis® or Kinzal®); Valsartan (Diovan®), and combinations thereof.

D. Pharmaceutical Compositions

Pharmaceutical compositions containing one or more EET antagonists and one or more AT1 antagonists are provided. In some embodiments, the compositions include a treatment for diabetes, including for example insulin or metformin.

The pharmaceutical compositions containing the antagonists can be formulated for administration by parenteral (intramuscular, intraperitoneal, intravitreally, intravenous (IV) or subcutaneous injection), transdermal (either passively or using iontophoresis or electroporation), or transmucosal (nasal, vaginal, rectal, or sublingual) routes of administration or using bioerodible inserts including ocular inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate diabetic retinopathy or one or more symptoms of the diabetic retinopathy. The precise dosage will vary according to a variety of factors such as subject-dependent variables (e.g., age, immune system health, etc.).

For the compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the compositions are administered locally, for example by injection directly into the eye by intravitreal injection or delivery. Typically, the injection causes an increased localized concentration of the composition which is greater than that which can be achieved by systemic administration. The compositions can be combined with a matrix assist in creating an increased localized concentration of the compositions by reducing the passive diffusion of the compositions out of the site to be treated.

E. Formulations

1. Formulations for Parenteral Administration

In some embodiments, the compositions disclosed herein are formulated in an aqueous solution for parenteral injection. A preferred route of administration is intravitreal administration. The formulation may also be in the form of a suspension or emulsion. In general, pharmaceutical compositions are provided including effective amounts of an EET antagonist and an AT1 antagonist, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

In some embodiments the compositions are formulated for enteral administration including oral, sublingual, and rectal delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The EET and AT1 antagonists can be chemically modified so that enteral delivery of the modified form is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for enteral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For enteral formulations, the location of release may be the stomach, the small intestine (the duodenum, the jejunem, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

The disclosed immunomodulatory agents can be applied topically. Topical administration does not work well for most peptide formulations, although it can be effective especially if applied to the eye, lungs, nasal, oral (sublingual, buccal), vaginal, or rectal mucosa.

One embodiment provides an eye drop formulation of administering the compositions to the eye.

Another embodiment provides an ophthalmic formulation for application to the eye, for example an eye drop, ointment or cream suitable for administration to the eye.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be cross-linked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Use

A. Subjects to be Treated

The disclosed compositions and methods are useful for treating diabetic retinopathy or symptoms thereof. Accordingly, exemplary subjects to be treated have been diagnosed with diabetes or have been determined to have a risk or predisposition of developing diabetes. The subject can have or be predisposed to have diabetes type 1 or diabetes type 2.

B. Methods of Treatment

The disclosed compositions can be used to treat diabetic retinopathy in subjects diagnosed with or having a predisposition to develop diabetes type 1 or diabetes type 2.

One embodiment provides a method of treating diabetic retinopathy in a subject thereof by administering to the subject one or more of the disclosed compositions to treat retinopathy, for example to improve visual acuity in a subject in need thereof.

Another embodiment provides a method of inhibiting or reducing the progression of diabetic retinopathy in a subject in need thereof by administering to the subject one or more of the disclosed, compositions to inhibit or reduce the progression of diabetic retinopathy.

In some embodiments, the compositions can be used to treat or inhibit one or more symptoms of diabetic retinopathy. Symptoms of diabetic retinopathy, include but are not limited to spots or dark strings floating in the field of vision, blurred vision, fluctuating vision, impaired color vision, dark or empty areas in the field of vision.

One embodiment provides a method for inhibiting or delaying the onset of diabetic retinopathy in a subject in need thereof by administering one or more of the disclosed compounds to inhibit or delay the onset of diabetic retinopathy.

The disclosed methods include administering the compositions parenterally or enterally. In one embodiment the disclosed methods include administering one or more of the disclosed compositions intravitreally.

In some of the disclosed methods, the EET antagonist and AT1 antagonist can be administered separately, contemporaneously, in alternation, or as a single unit dose.

In some embodiments the disclosed compositions and methods can be used in combination with one or more treatments for diabetes. Exemplary treatments for diabetes include, but are not limited to insulin or metformin treatment or administration.

EXAMPLES

Example 1 sEH Inhibition Reduces Blood Pressure in Ang II-Induced Hypertension

Methods and Materials

Eight-week-old male B6 mice were treated for 4 weeks with Ang II (3 mg/kg/day, s.c.; Alzet)+t-AUCB (40 mg/L in drinking water; Cayman), Ang II (Sigma), or vehicle. Trans-4-[4-(3-adamantan-1-ylureido)-cyclohexyloxyl]-benzoic acid (t-AUCB) is a selective inhibitor of soluble epoxide hydrolase with an $IC_{50}$=8 nM of sEH (Liu, et al, Br. J. Pharmacol., 156:284-296 (2009)) . ($K_i$=2 nM to human sEH in vitro (Lorthioir, A., et al., Cardiovasc Hematol Agents Med Chem., 10:212-222 (2012)).

Results

Mice injected with Ang II became hypertensive (FIG. 1A). In contrast, treatment with t-AUCB significantly reduced blood pressure (FIG. 1A), suggesting that sEH blockade has an antihypertensive effect. These results are consistent with previous reports that sEH inhibition reduces blood pressure in Ang II-induced hypertension.

Example 2

Ang II Induces Retinal sEH Expression

Methods and Materials

Mice were treated as described in Example 1.

The expression of albumin, ICAM-1, IL-6, GADPH, GLUT-1, and sEH was analyzed by homogenization of tissues or cells. Samples from mice in different treatments as well as human retinal endothelial cells (HRECs) were separated by electrophoresis for 3 h. The proteins were transferred to an enhanced chemiluminescence (ECL) membrane in a transfer buffer. The membranes were blocked for 90 min with 5% nonfat dry milk in Tris-buffered saline. The membranes were incubated with antibody against albumin (1:5000; Bethyl), ICAM-1 (1:2000; Cell Signaling), IL-6 (1:2000; Santa Cruz), GADPH (1:2000; abeam), GLUT-1 (1:10,000; abeam), or sEH (1:500; Santa. Cruz). The membranes were incubated with secondary antibody for albumin, ICAM-1, IL-6, GADPH, GLUT-1, or sEH. Chemiluminescent detection using ECL reagent from Millipore Corporation was done on X-ray film. In addition, quantification of the expression levels of these proteins was analyzed with NIH image J software.

Results

Figure 1B:
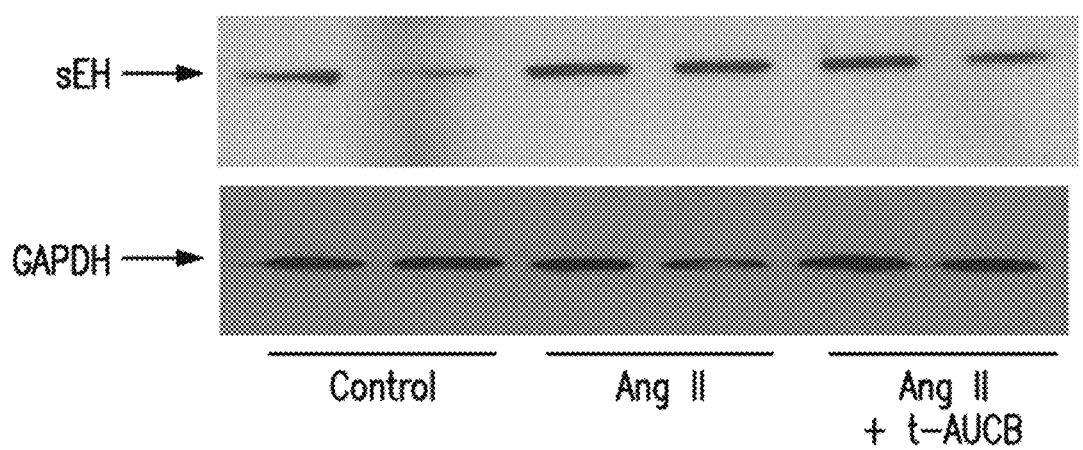
FIG. 1B is an autoradiograph of a Western blot showing sEH and GAPDH in control mice, mice treated with Ang II, and mice treated with Ang II+t-AUCB.
Figure 1C:
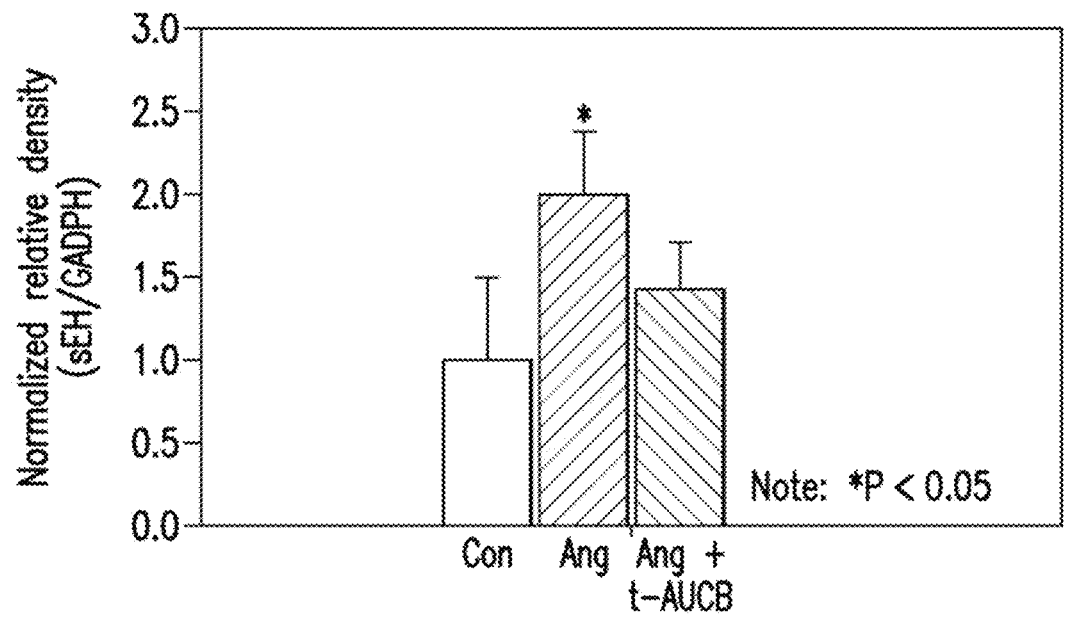
FIG. 1C is a bar graph of normalized relative density (sEH/GAPDH) in control mice (clear rectangle), mice treated with Ang II (black rectangle), and mice treated with Ang II+t-AUCB (grey rectangle).

Retinal sEH protein levels were elevated 2 fold in the Ang II group as compared with the vehicle group (FIGS. 1B and 1C, see arrow). The mechanism whereby Ang II induces retinal sEH expression is still not known, but this result is consistent with previous reports that Ang II infusion stimulates she expression in the kidneys and heart.

Example 3 sEH Blockade Significantly Increased Total Albumin

Methods and Materials

Mice were treated as described in Example 1.

The expression of albumin, ICAM-1 IL-6, GADPH, GLUT-1, and sEH was analyzed by homogenization of tissues or cells. Samples from mice in different treatments as well as human retinal endothelial cells (HRECs) were separated by electrophoresis for 3 h. The proteins were transferred to an enhanced chemiluminescence (ECL) membrane in a transfer buffer. The membranes were blocked for 90 min with 5% nonfat dry milk in Tris-buffered saline. The membranes were incubated with antibody against albumin (1:5000; Bethyl), ICAM-1 (1:2000; Cell Signaling), IL-6 (1:2000; Santa Cruz), GADPH (1:2000; abcam), GLUT-1 (1:10,000; abcam), or sEH (1:500; Santa Cruz). The membranes were incubated with secondary antibody for albumin, ICAM-1, IL-6, GADPH, GLUT-1, or sEH. Chemiluminescent detection using ECL reagent from Millipore Corporation was done on X-ray film. In addition, quantification of the expression levels of these proteins was analyzed with NIH image J software.

Results

Figure 1D:
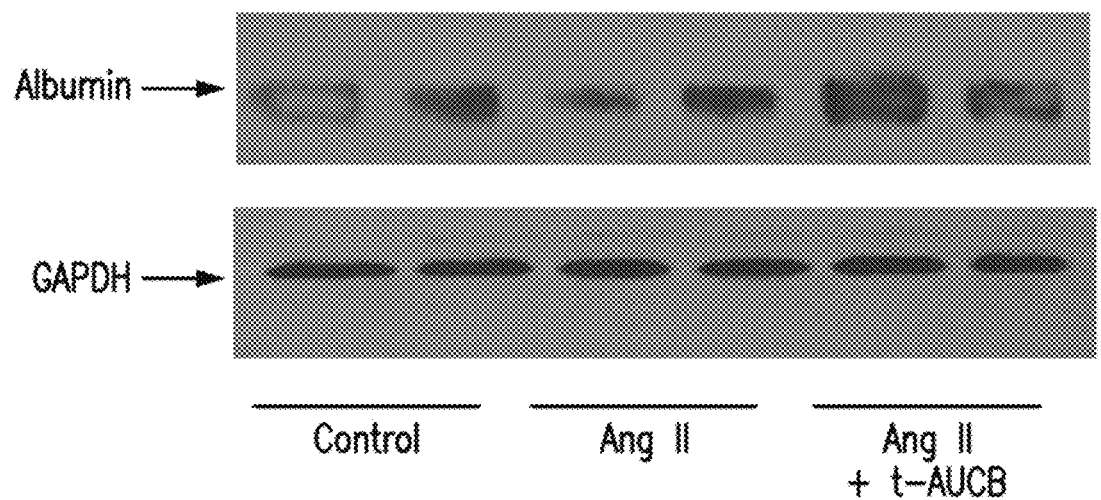
FIG. 1D is an autoradiograph of a Western blot of albumin and GAPDH in control mice, mice treated with Ang II, and mice treated with Ang II+t-AUCB.
Figure 1E:
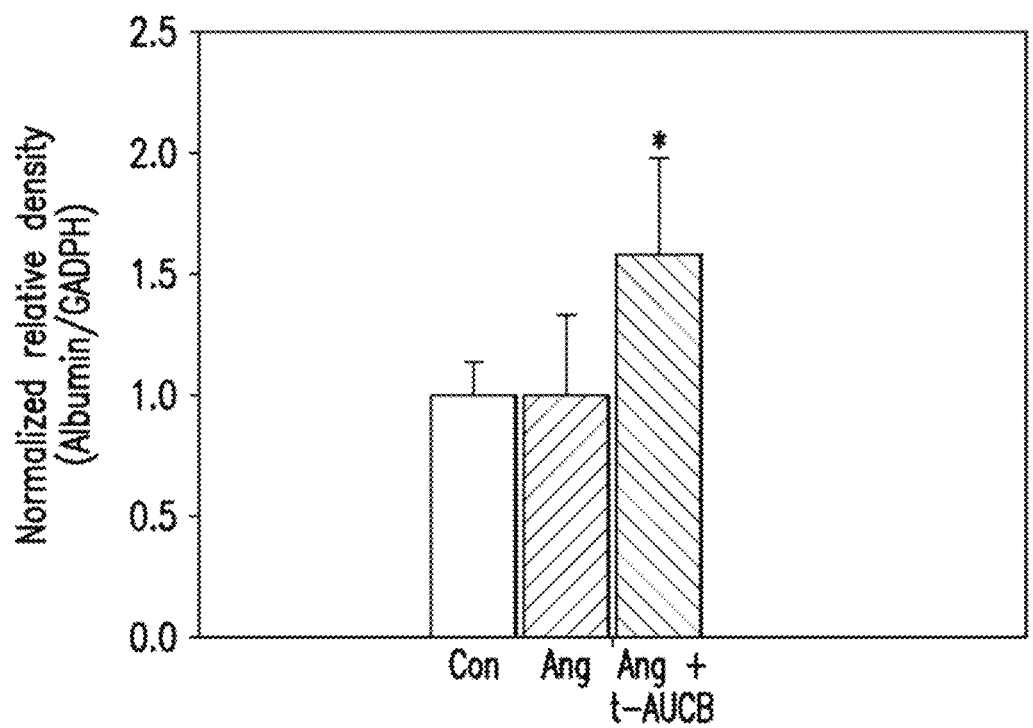
FIG. 1E is a bar graph of normalized relative density (Albumin/GAPDH) for mice treated with vehicle (clear rectangle), mice treated with Ang II (black rectangle), and mice treated with AngII+t-AUCB (grey rectangle).
Figure 1F:
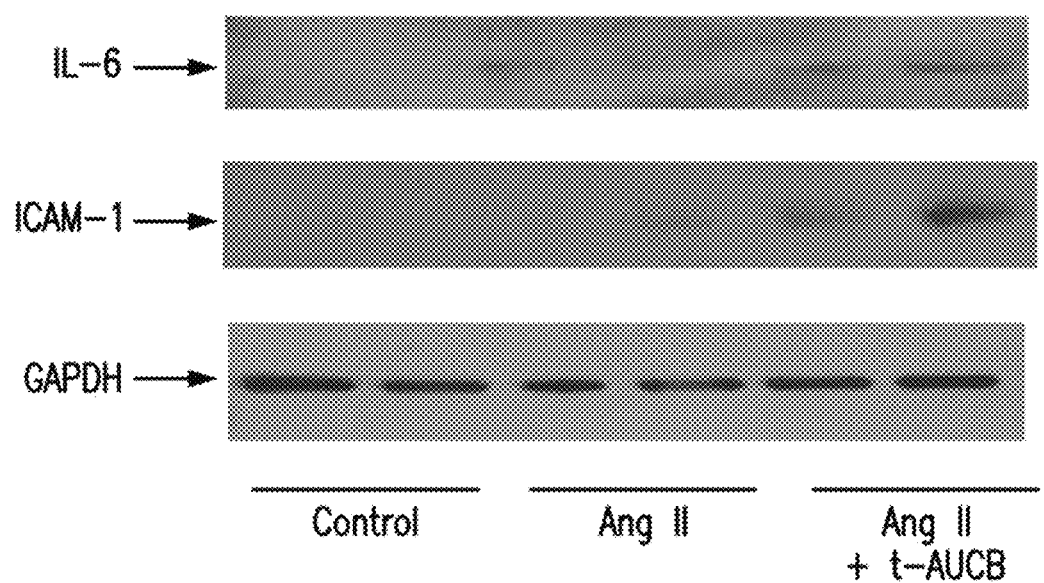
FIG. 1F is a autoradiograph of a Western blot for ICAM-1, IL-6, and GAPDH for control mice, mice treated with Ang II, and mice treated with Ang II+t-AUCB.

To explore the role of sEH blockade in Ang II-induced retinal permeability, total retinal albumin content was determined. Notably, Ang II did not affect total retinal albumin, whereas sEH blockade significantly increased total albumin in the retinas of Ang II±t-AUCB mice (FIGS. 1D and 1E). Moreover, sEH blockade promoted Ang II-induced retinal expression of ICAM-1 and IL-6, which are inflammatory mediators (FIG. 1F).

Example 4

Ang II Infusion Increased Retinal Expression of sHE

Methods and Materials

Male mice were treated for 4 weeks with Ang II (3 mg/kg/day, s.c.; Alzet)+telmisartan, a selective AT1 antagonist (2.5 mg/kg/day in drinking water; Cayman), Ang II, or vehicle.

The expression of albumin, ICAM-1, IL-6, GADPH, GLUT-1, and sEH was analyzed by homogenization of tissues or cells. Samples from mice in different treatments as well as human retinal endothelial cells (HRECs) were separated by electrophoresis for 3 h. The proteins were transferred to an enhanced chemiluminescence (ECL) membrane in a transfer buffer. The membranes were blocked for 90 min with 5% nonfat dry milk in Tris-buffered saline. The membranes were incubated with antibody against albumin (1:5000; Bethyl), ICAM-1 (1:2000; Cell Signaling), IL-6 (1:2000; Santa Cruz), GADPH (1:2000; abcam), GLUT-1 (1:10,000; abcam), or sEH (1:500; Santa Cruz). The membranes were incubated with secondary antibody for albumin, ICAM-1, IL-6, GADPH, GLUT-1, or sEH. Chemiluminescent detection using ECL reagent from Millipore Corporation was done on X-ray film. In addition, quantification of the expression levels of these proteins was analyzed with NIH image J software.

Results

Figure 1G:
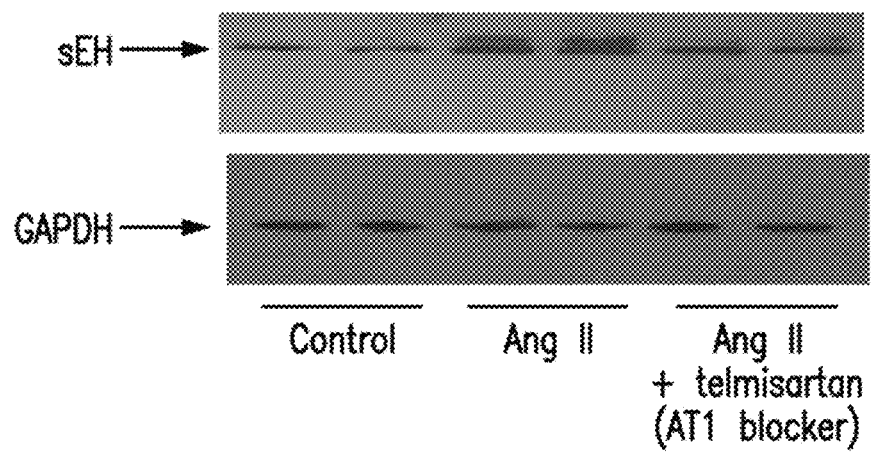
FIG. 1G is autoradiograph of sEH and GAPDH for control mice, mice treated with Ang II, and mice Ang II+AT1 blocker.
Figure 1H:
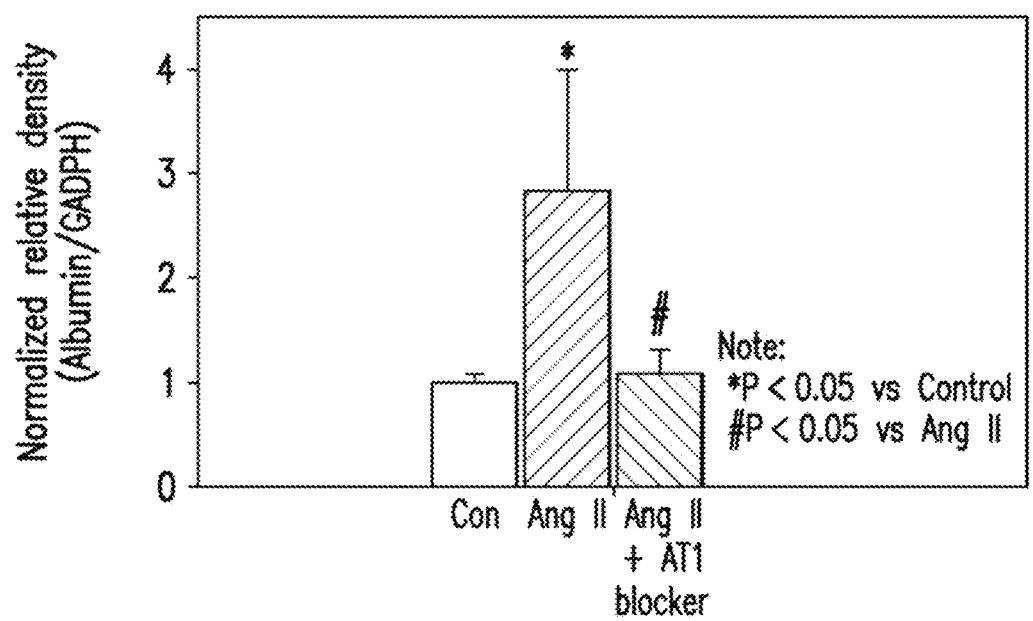
FIG. 1H is a bar graph of normalized relative density for control mice treated with vehicle, mice treated with Ang II, and mice treated with Ang II+AT1 blocker.
Figure 2A:
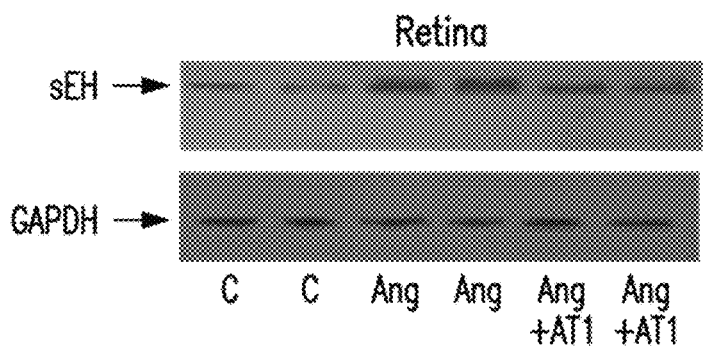
FIGS. 2A-2C are autoradiographs showing sEH and GAPDH proteins in different tissues in control mice treated with vehicle, mice treated with Ang II, and mice treated with Ang II+AT1 blocker.
Figure 2B:
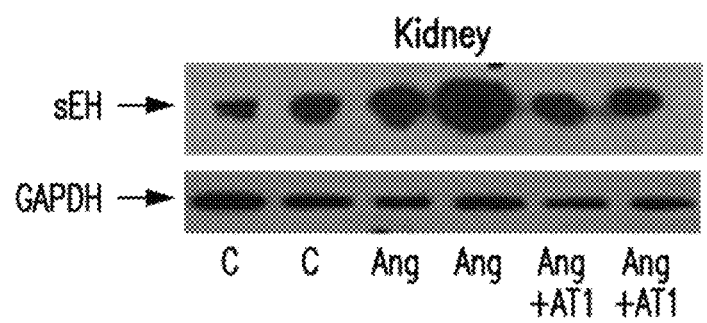
Figure 2C:
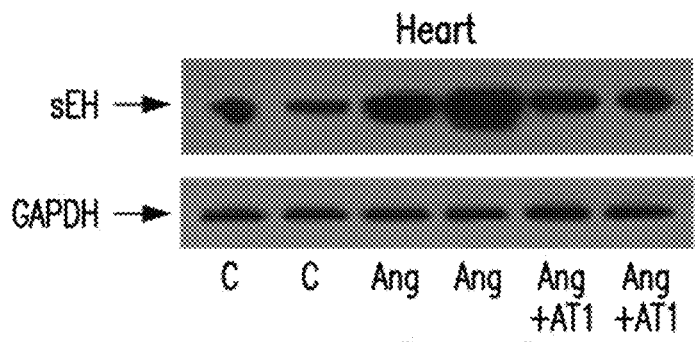
Figure 2D:
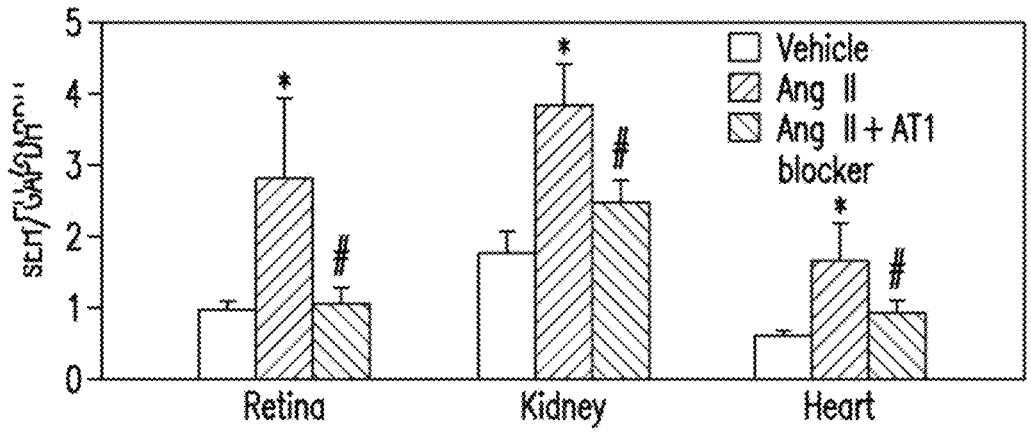
FIG. 2D is a bar graph of normalized relative density of sEH/GAPDH for the autoradiographs of FIGS. 2A-2C.

Ang II infusion increased retinal expression of sEH, which was reversed by telmisartan (FIGS. 1G and 1H, 2A). Telmisartan also attenuated Ang II-induced sEH expression in the kidney (FIG. 2B) and heart (FIG. 2C). Collectively, these data demonstrate that Ang II augments retinal sEH levels through the AT1 receptor.

Example 5 sEH KO Affects Ang II-Induced Retinal Damage

Methods and Materials

Well-defined sEH (Ephx2) Knock Out (KO) mice were used as described (Luo, P., et al., J Pharmacol Exp Ther., 334:430-438 (2010). sEH (−/−) and sEH (+/+) mice into the following treatment groups: sEH (−/−)+Ang II, sEH (+/+)+Ang II, and sEH (+/+)+vehicle, then treated them for 4 weeks.

The expression of albumin, ICAM-1, IL-6, GADPH, GLUT-1, and sEH was analyzed by homogenization of tissues or cells. Samples from mice in different treatments as well as human retinal endothelial cells (HRECs) were separated by electrophoresis for 3 h. The proteins were transferred to an enhanced chemiluminescence (ECL) membrane in a transfer buffer. The membranes were blocked for 90 min with 5% nonfat dry milk in Tris-buffered saline. The membranes were incubated with antibody against albumin (1:5000; Bethyl), ICAM-1 (1:2000; Cell Signaling), IL-6 (1:2000; Santa Cruz), GADPH (1:2000; abcam), GLUT-1

(1:10,000; abcam), or sEH (1:500; Santa Cruz). The membranes were incubated with secondary antibody for albumin, ICAM-1, IL-6, GADPH, GLUT-1, or sEH. Chemiluminescent detection using ECL reagent from Millipore Corporation was done on X-ray film. In addition, quantification of the expression levels of these proteins was analyzed with NIH image J software.

Results

Figure 3A:
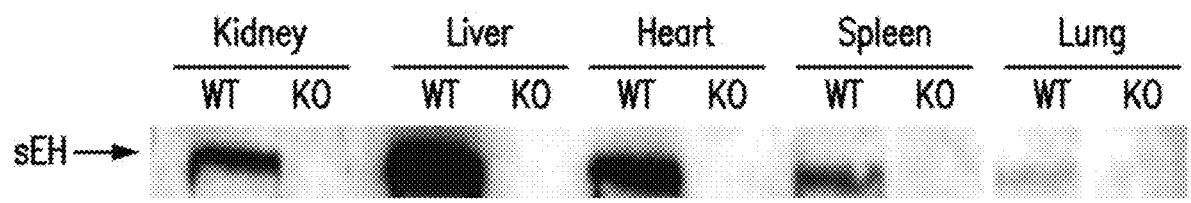
FIGS. 3A and 3B are autoradiographs showing sEH protein is expressed in different tissues in Ephx3 KO mice.
Figure 3B:
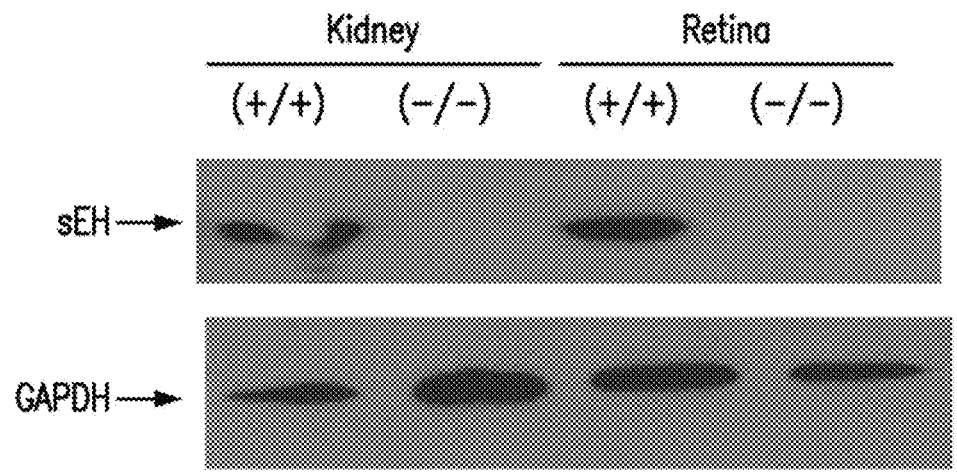
Figure 3C:
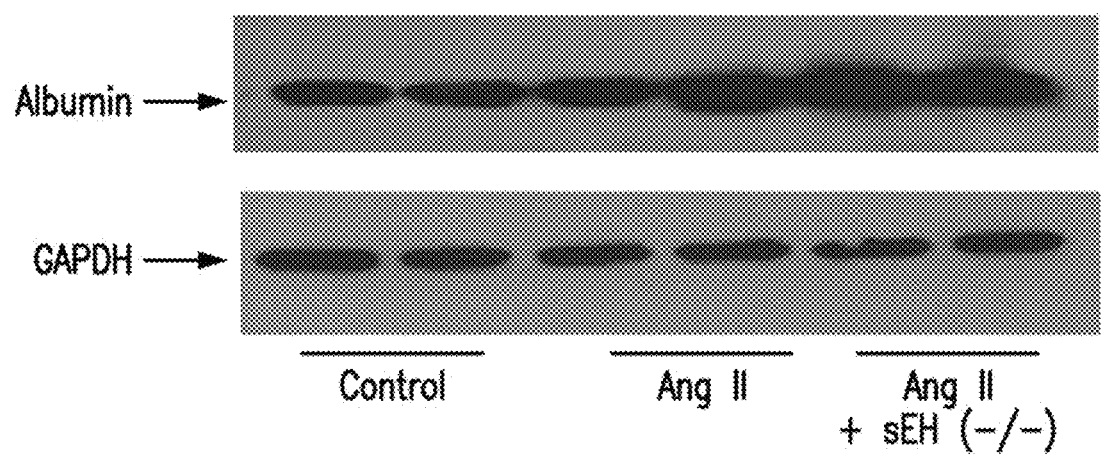
FIG. 3C is an autoradiograph of albumin and GAPDH protein levels in retinas of KO mice treated with Ang II.
Figure 3D:
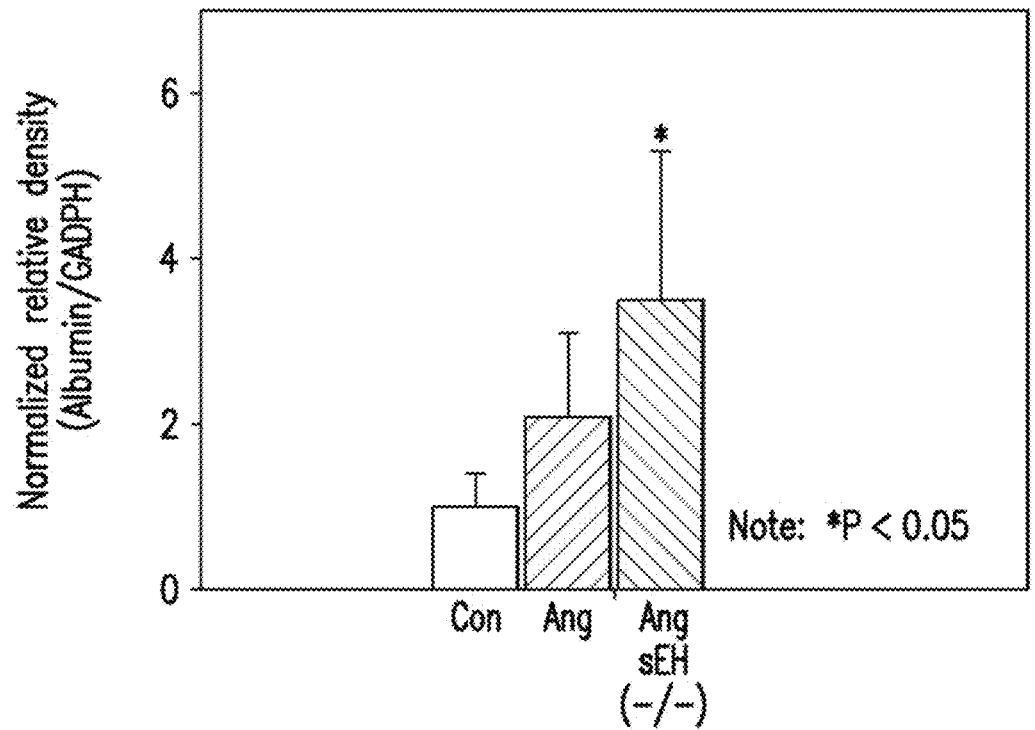
FIG. 3D is a bar graph of normalized relative density (Albumin/GAPDH) in sEH (+/+) mice treated with vehicle (clear rectangle), sEH (+/+) mice treated with Ang II (black rectangle), and sEH (−/−) mice treated with Ang II.

As shown in FIGS. 3A and 3B, sEH protein is expressed in different tissues, including the retina, of sEH (+/+) mice, but is absent in sEH (−/−) mice. sEH KO resulted in a 3-fold increase in total albumin in the retinas of sEH (−/−)+Ang II mice relative to levels in wild-type mice (FIGS. 3C and 3D), suggesting that deletion of sEH leads to retinal hyperpermeability.

Example 6

Effect of Intravitreal Injection of Angiotensin II and EETs on Total Retinal Albumin Methods and Materials B6 Mice were injected mice with Ang II (1 or 5 µg per eye) or vehicle assayed for albumin leakage. The expression of albumin was used as the index of leakage assay. Mice were treated with 11, 12-EET (15 µg/kg/day, s.c.; Alzet: Cayman), 14,15-EET (15 µg/kg/day, s.c.; Alzet; Cayman), or vehicle. 11,12-EET and 14,15-EET were used because they are the major products of cytochrome P450 (CYP) epoxygenases. On day 3 after treatment, mice were intravitreally injected with Ang II (5 µg/µl).

Results

Figure 4A:
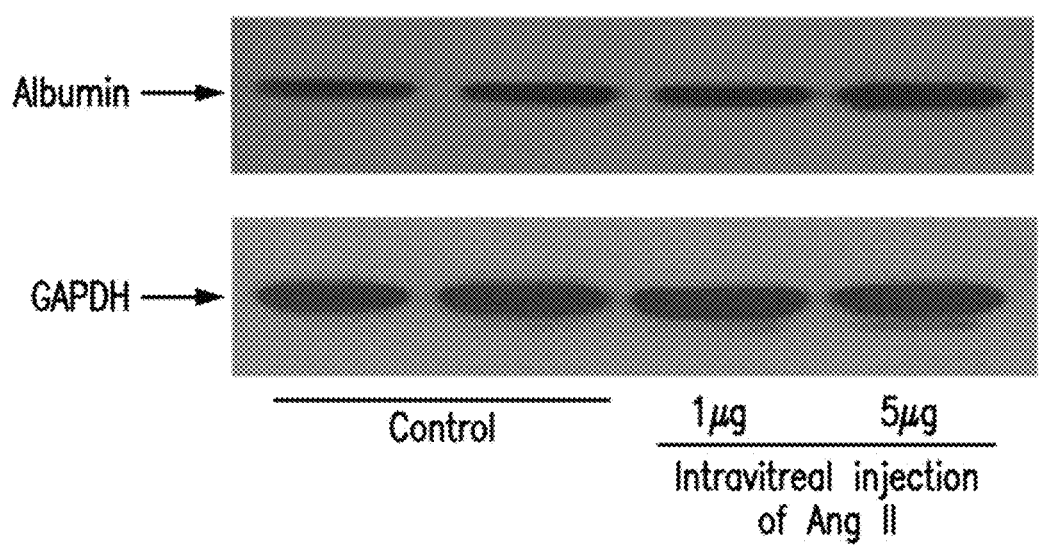
FIG. 4A is an autoradiograph of a Western blot for albumin and GAPDH in mice intravitreally injected with angiotensin II and EETs.
Figure 4B:
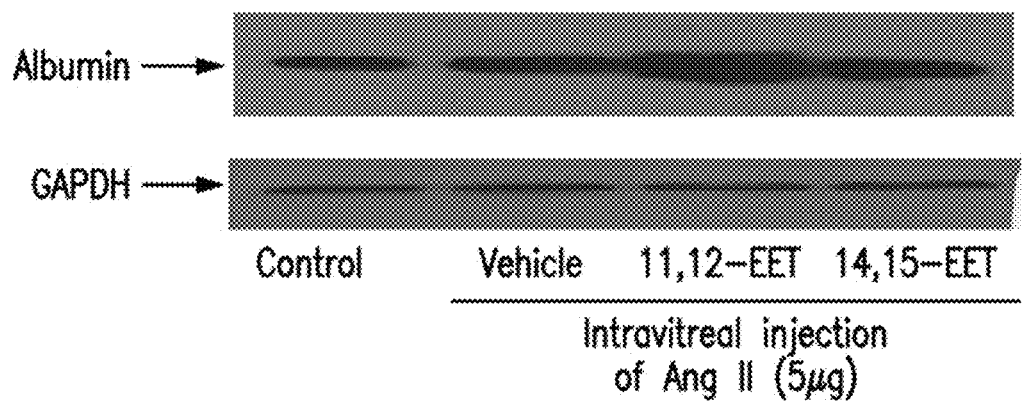
FIG. 4B is an autoradiograph of a Western blot for albumin and GAPDH in mice intravitreally injected with 11,12-EET or 14, 15 EET and angiotensin II.
Figure 4C:
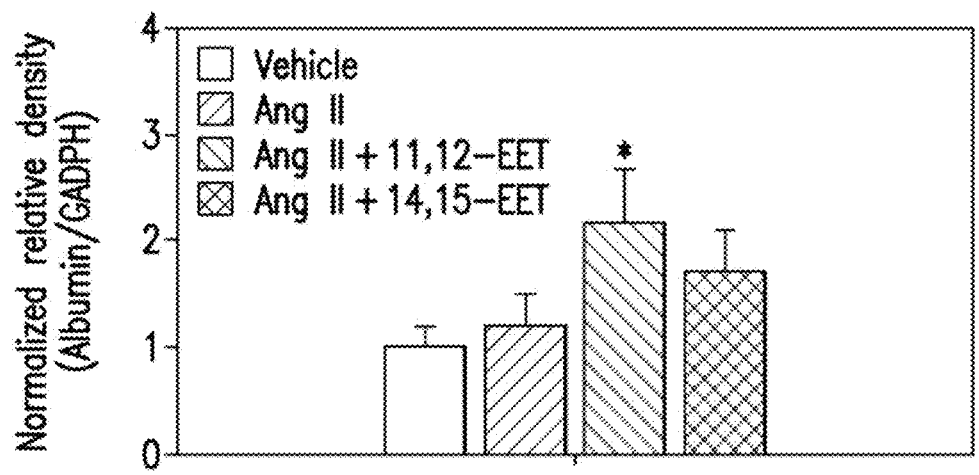
FIG. 4C is a bar graph of normalized relative density (Albumin/GAPDH) for mice intravitreally treated with vehicle (clear rectangle), Aug II (black rectangle), Ang II+11,12-EET (grey rectangle), or Ang II+14,15-EET (stippled rectangle).

Notably, although both 11,12-EET and 14,15-EET promoted intravitreal Ang II-induced retinal albumin leakage (FIG. 4B), that leakage attained significance only with injection of 11,12-EET (FIG. 4C). This result directly demonstrates that 11,12-EET is more potent than 14,15-EET in potentiating intravitreal Ang II-induced retinal damage.

Example 7

Chronic Hyperglycemia Causes Elevation of Plasma Levels of 14,15-EET and DHETs

Methods and Materials

Male 96 mice were treated with STZ (55 mg/kg/day, i.p.) for 5 consecutive days. Mice were considered diabetic when their plasma glucose levels exceeded 300 mg/dL. The circulating lipidomic profiles of various polyunsaturated fatty acids including linoleic acid (LA), arachidonic acid (AA), eicosapentaenoic acid (EPA), and docosahexaenoic acid (DHA) were determined by different metabolizing enzymes, including 12/15-LO, COX, CYP, and sEH in diabetic and nondiabetic mice. Six months after the establishment of diabetes, a clustered heat map of bioactive lipid metabolites was obtained in these animals.

Lipidomic analysis was done by LC/MS in Lipidomics Core Facility (Wayne State University, Detroit, Mich.). Briefly, plasma samples were spiked with 10 ng of 15(S)-HETE-d8, Leukotriene B4-d4, and Prostaglandin E1-d4 as internal standards for recovery and quantitation. The spiked samples were mixed thoroughly and then loaded on C18 columns for extracting polyunsaturated fatty acid (PUFA) metabolites. LC-MS analysis was performed on a Prominence XR system (Shimadzu) using Luna C18 (3µ, 2.1×150 mm) column. The mobile phase consisted of a gradient between A: methanol-water-acetonitrile (10:85:5 v/v) and B: methanol-water-acetonitrile (90:5:5 v/v), both containing 0.1% ammonium acetate. The gradient program with respect to the composition of B was as follows: 0-1 min, 50%; 1-8 min, 50-80%; 8-15 min, 80-95%; and 15-17 min, 95%. The flow rate was 0.2 ml/min. The eluate was directly introduced to ESI source of QTRAP5500 mass analyzer (ABSCIEX) in the negative ion mode with following conditions: Curtain gas: 35 psi, GS1: 35 psi, GS2: 65 psi, Temperature: 600° C., Ion Spray Voltage: −1500 V, Collision gas: low, Declustering Potential: −60 V, and Entrance Potential: −7 V. The eluate was monitored by Multiple Reaction Monitoring (MRM) method to detect unique molecular ion—daughter ion combinations. Optimized Collisional Energies (18-35 eV) and Collision Cell Exit Potentials (7-10 V) were used for each MRM transition. The data was collected using Analyst 1.5.2 software and the MRM transition chromatograms were quantitated by MultiQuant software (both from ABSCIEX). The internal standard (15-HETE-d8) signal in each chromatogram was used for normalization for recovery as well as relative quantitation of each analyte. Then, metabolite concentrations were normalized to the total plasma protein content. Matrix2png Viewer (http://www.chibi.ubc.ca/matrix2png/) was used to analyze and represent the lipid metabolomic data as a heat map.)

Results

Figures 1, 5A:
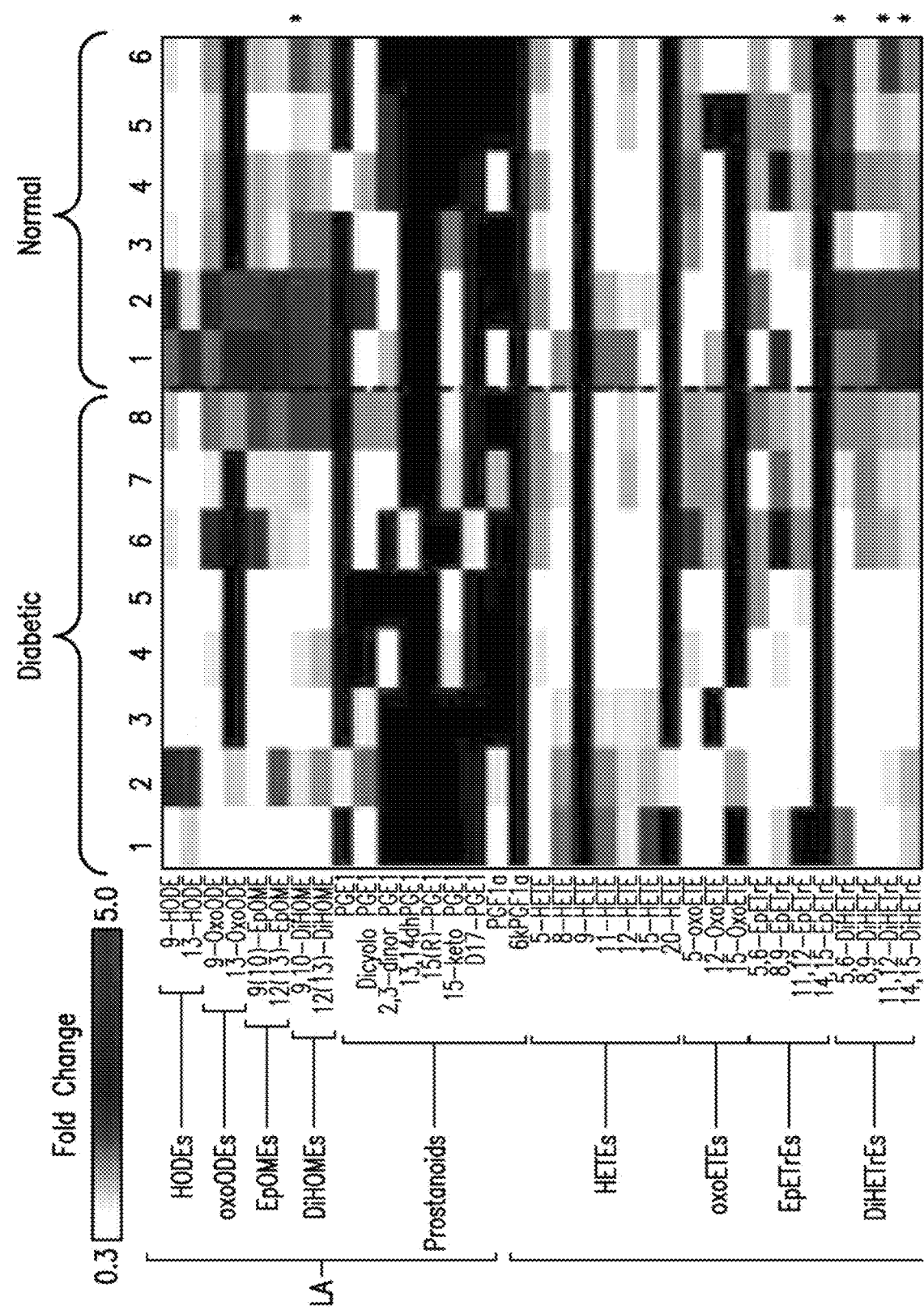
FIG. 5A is a heat map of bioactive lipid metabolites in treated mice. The metabolites were initially clustered into four major groups according to their polyunsaturated fatty acid (PUFA) origin; linoleic acid (LA), arachidonic acid (AA), eicosapentaenoic acid (EPA), or docosahexaenoic acid (DHA). This primary clustering is followed by secondary subclustering bioactive lipid metabolites within each PUFA group according to their putative enzymatic biosynthesis pathways and hence chemical structure similarity. The LA group includes the following subclusters: hydroxyoctadecadienoic acids (HODEs), oxooctadecadienoic acids (oxoODEs), epoxyoctadecamonoenoic acids (EpOME), dihydroxyoctadecamonoenoic acids (DiHOME), and LA-derived 1-series prostanoids. The AA group includes: hydroxyeicosatetraenoic acids (HETEs), oxoeicosatetraenoic acids (oxoETEs), epoxyeicosatrienoic acids (EpETrEs), Dihydroxyeicosatrienoic acids (DiHETrEs), AA-derived 4-series leukotrienes (LTs), AA-derived 4-series lipoxins (LXs), and AA-derived 2-series prostanoids and thromboxane (TXs). The EPA group includes: hydroxyeicosapentaenoic acids (HEPEs), epoxyeicosatetraenoic acids (EpETEs), dihydroxyeicosatetraenoic acids (DiHETEs), EPA-derived 5-series LTs, EPA-derived 5-series LXs, EPA-derived 3-series prostanoids, and E-series Resolvins (Rvs). The DHA group includes: hydroxydecosahexaenoic acids (HDoHEs), epoxydecosapentaenoic acids (EpDOPEs), Dihydroxydecosapentaenoic acids (DIHDOPEs), and D-series Rvs. The significant (P<0.05) increased metabolites (9,10-DiHOME, 5,6-DiHETrE, 11,12-DiHETrE, 14,15-DiHETrE, 15d-D12,14-PGJ3, and RvD2) were indicated by * while decreased metabolites were indicated by #. Data shown for the comparison are the fold change of 6 diabetic and 8 nondiabetic mice relative to the average of nondiabetic mice±SD.
Figures 2, 5A:
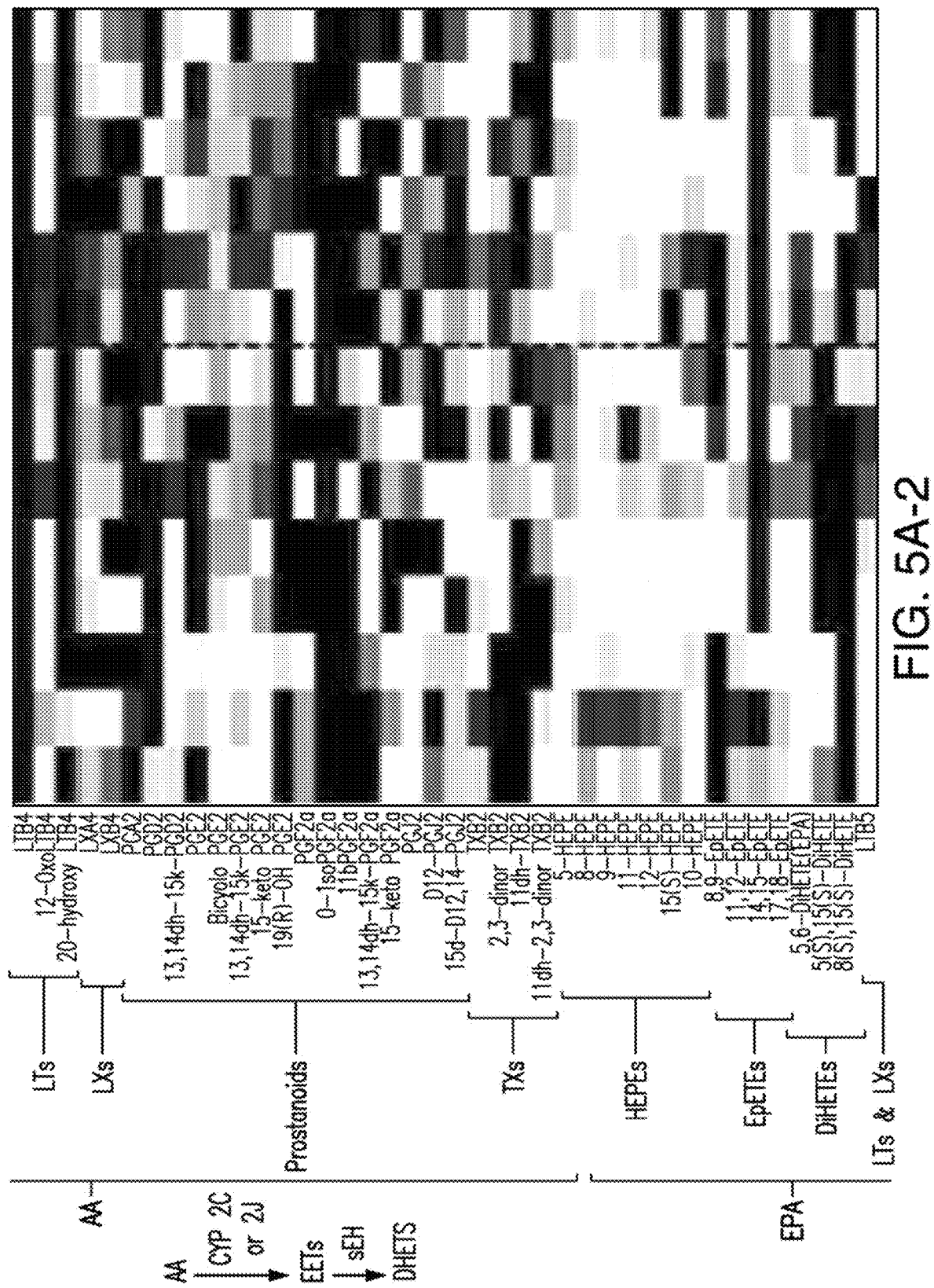
Figures 3, 5A:
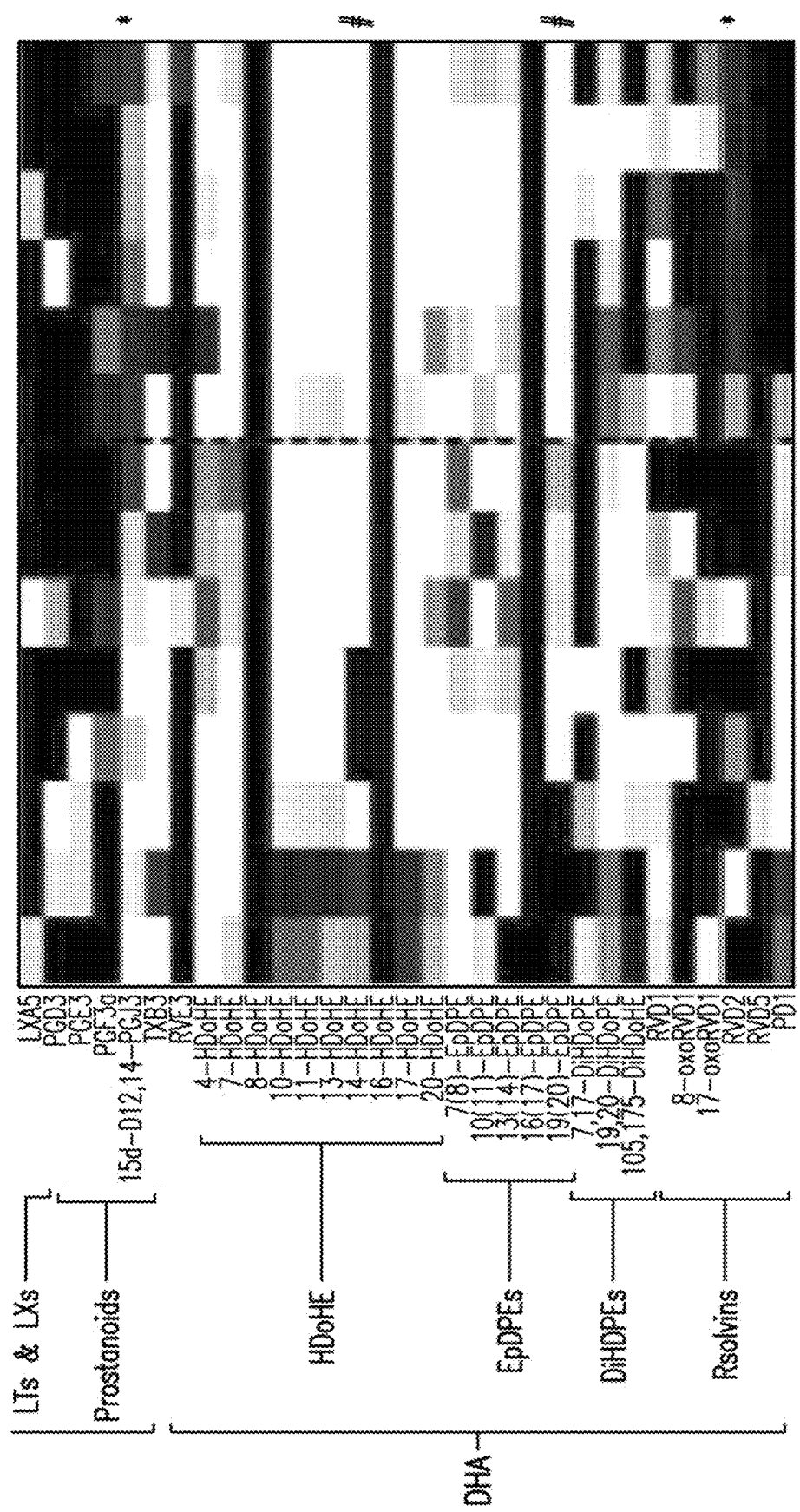
Figure 5B:
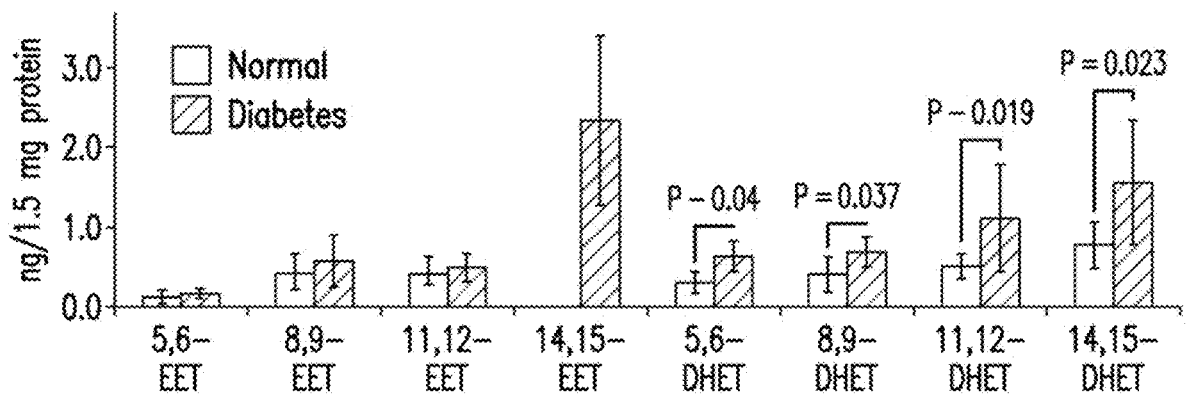
FIG. 5B is a bar graph of ng/1.5 mg (protein) of plasma EETs and DHETs in control mice (clear rectangle) and diabetic mice (black rectangle).

FIG. 4A shows a heat map of bioactive lipid metabolites in treated mice. Statistical analysis showed that of the 107 bioactive lipids screened, only 6 lipids were significantly increased. These were 5,6-DHET; 11,12-DHET; 14,15-DHET; 9,10-dihydroxyoctadecamonoenoic (DiHOME), 15d-D12; 14-PG J3, and Resolvin (rv) D2. Among these, the three lipids (DHETs) are metabolites of the EETs/sEH pathway. To verify the results of circulating lipidomic analysis, plasma levels of EETs and DHETs were determined by LC/MS/MS in diabetic and control mice. It was found that, as compared with control mice, the levels of 5,6-DHET, 8,9-DHET, 11,12-DHET, 14,15-DHET, and 14,15-EET in diabetic mice were significantly elevated (FIG. 5B), suggesting that the circulating lipidomic profile in diabetes was dominated by EETs/sEH products. Since 14,15-EET is a proangiogenic lipid mediator, elevated 14,15-EET levels are believed to contribute to diabetes-induced retinal microvascular dysfunction.

Example 8

Hyperactivity of RAS in Diabetes Up-Regulates Retinal sEH, and sEH KO Potentiates Diabetes-Induced Retinal Microvascular Damage Via Promoting VEGF and GLUT-1

Methods and Materials

Male sEH (−/−) and sEH (+/+) mice were divided into sEH (+/+), sEH (+/+)+STZ, and sEH (−/−)+STZ. Mice were treated with one high dose of STZ (200 mg/kg/day, i.p.), a model of type 1 diabetes. This protocol was used to exclude the anti-hyperglycemia function of sEH KO.

Figure 6A:
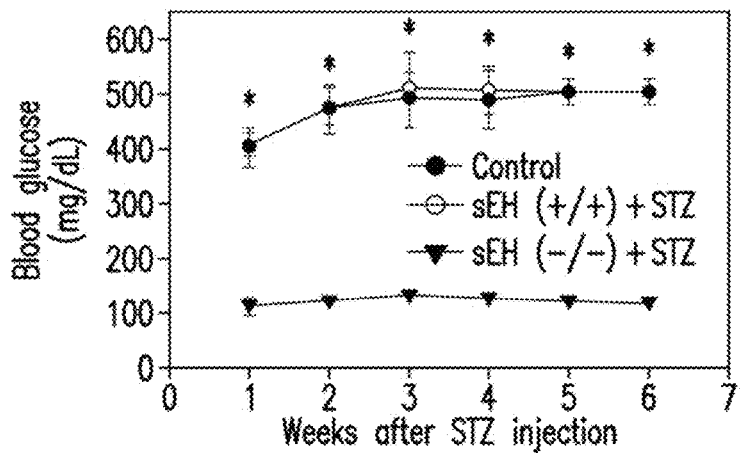
FIG. 6A is a line graph showing fasting blood glucose levels (mg/ml) in control mice (●), sEH +/+ mice treated with STZ (○), and sEH −/− mice treated with STZ (▼) over time (weeks).
Figure 6B:
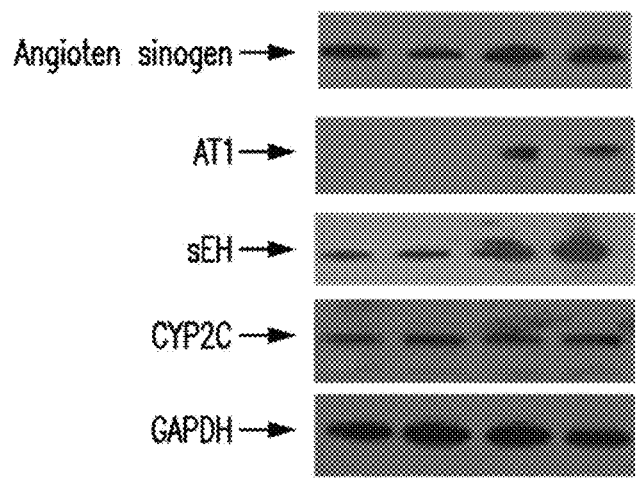
FIG. 6B are autoradiographs of angiotensinogen, AT1, sEH, CYP2C, and GAPDH proteins in retinas of sEH +/+ mice with or without STZ treatment.
Figure 7A:
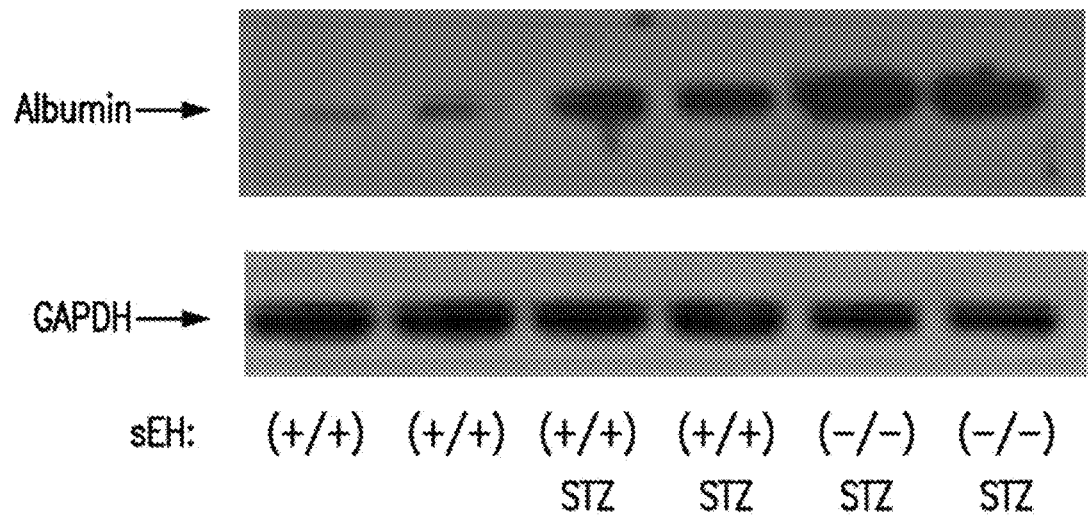
FIG. 7A is an autoradiograph of a Western blot for albumin and GAPDH proteins in wild-type mice (sEH +/+), wild-type mice+STZ, sEH KO mice+STZ.

Results sEH KO did not affect hyperglycemia in STZ mice (FIG. 6A). Diabetes caused elevated expression of Angiotensinogen and AT1 receptor, which supports the noting that RAS is activated in the retinas of STZ mice (FIG. 6B). Strikingly, RAS activation resulted in a 2.4-fold increase of retinal sEH levels (FIG. 6B). sEH KO caused a detrimental effect on retinal albumin in diabetic mice (FIG. 7A). diabetes caused a 38% decrease of retinal GLUT-1 expression, which is compatible with the results from an interesting report.

Figure 7B:
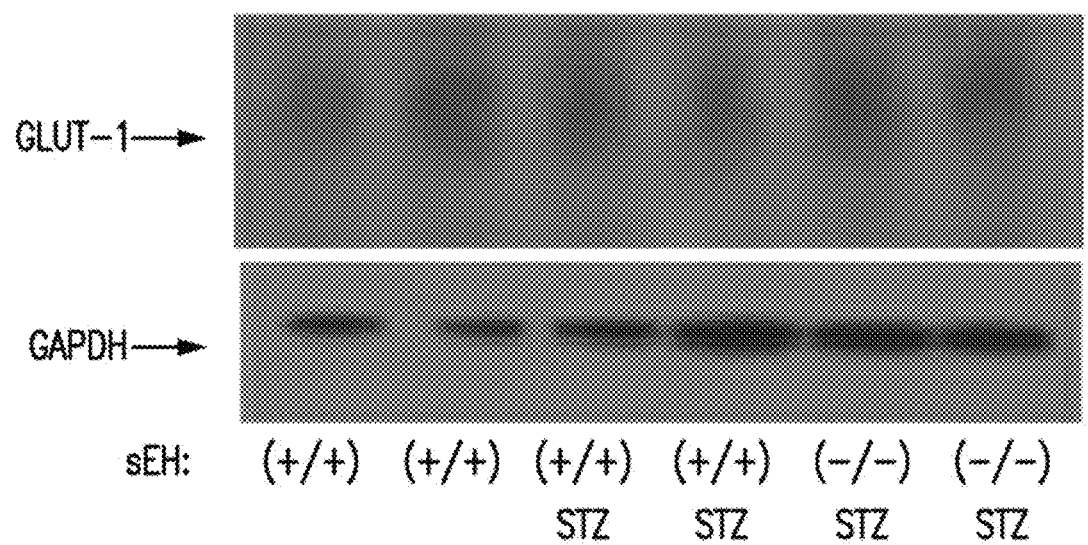
FIG. 7B is an autoradiograph of a Western blot for GLUT-1 and GAPDH proteins in sEH (+/+) mice, sEH (+/+) mice+STZ, sEH KO mice+STZ.
Figure 7C:
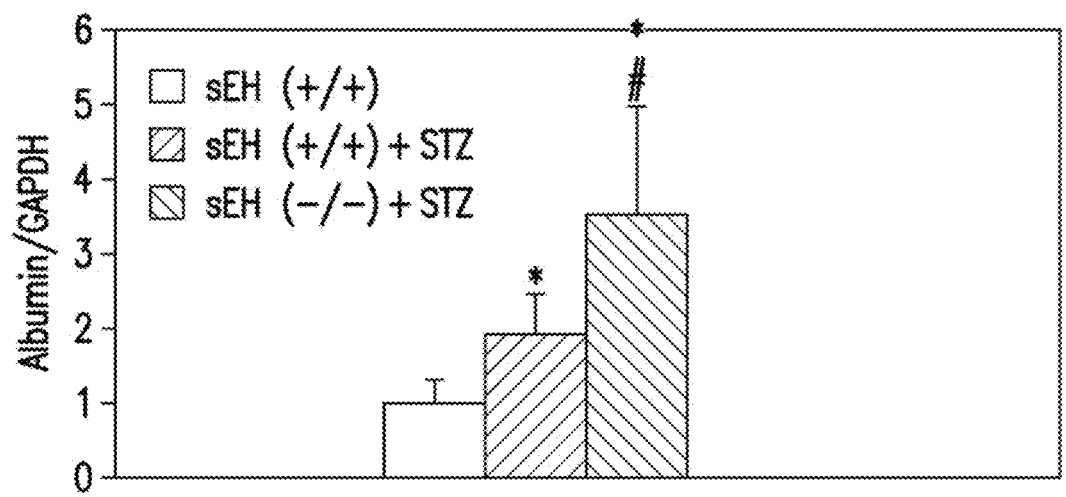
FIG. 7C is a bar graph of normalized relative density (albumin/GAPDH) from the autoradiograph of FIG. 7A, sEH (+/+) mice (white bars), sEH (+/+) mice+STZ (black bars), sEH KO mice+STZ (gray bars).
Figure 7D:
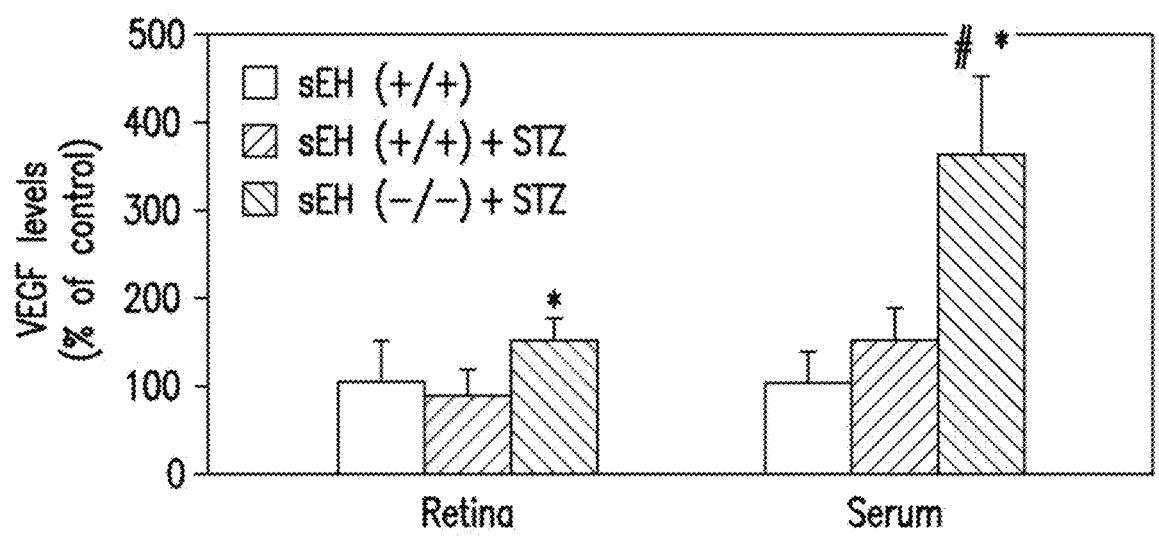
FIG. 7D is a bar graph showing retinal and serum levels of VEGF in sEH (+/+) mice (white bars), sEH (+/+) mice+STZ (black bars), sEH KO mice+STZ (gray bars).

Intriguingly, the reduction of retinal GLUT-1 expression by diabetes was effectively restored by sEH KO (FIG. 7B); and importantly, sEH KO augmented retinal and serum VEGF levels (FIG. 7C), which is consistent with previous studies, along with caused retinal vascular leakage in diabetic mice. Taken together, these findings suggest a potential molecular mechanism that sEH KO potentiates diabetes-induced retinal damage via promoting VEGF and GLUT-1.

Example 9 sEH KO Potentiates the Effects of 11,12-EET on Intravitreal hVEGF-Induced Retinal Microvascular Damage Materials and Methods sEH (−/−) and sEH (+/+) mice were treated with 11, 12-EET (15 µg/kg/day, s.c.; Alzet) or a vehicle for one week, then injected with hVEGF.

Results

Figure 8A:
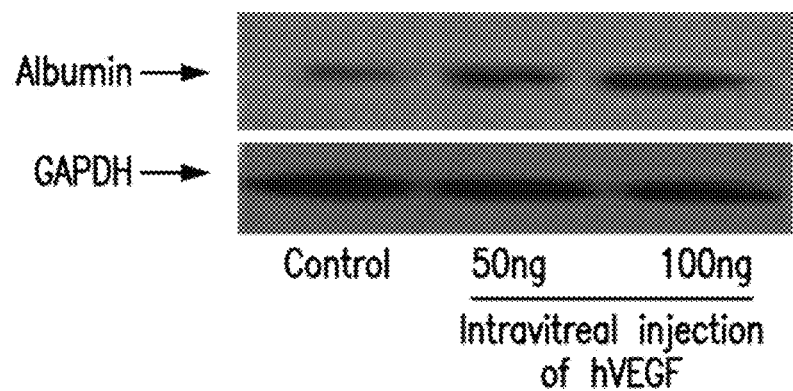
FIG. 8A is an autoradiograph of a Western blot for albumin and GAPDH proteins in mice injected intravitreally with recombinant human VEGF.
Figure 8B:
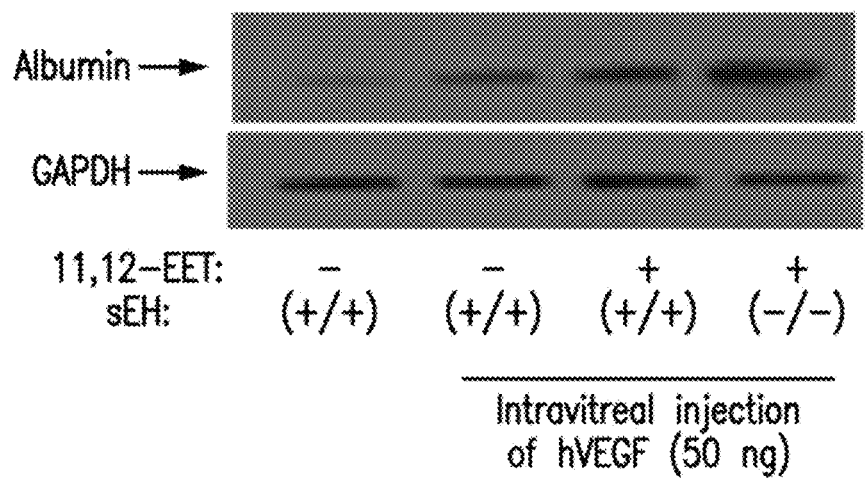
FIG. 8B is an autoradiograph of a Western blot for albumin and GAPDH proteins in sEH (+/+) mice and sEH KO mice treated with or without 11,12-EET and intravitreal injection of recombinant human VEGF.
Figure 8C:
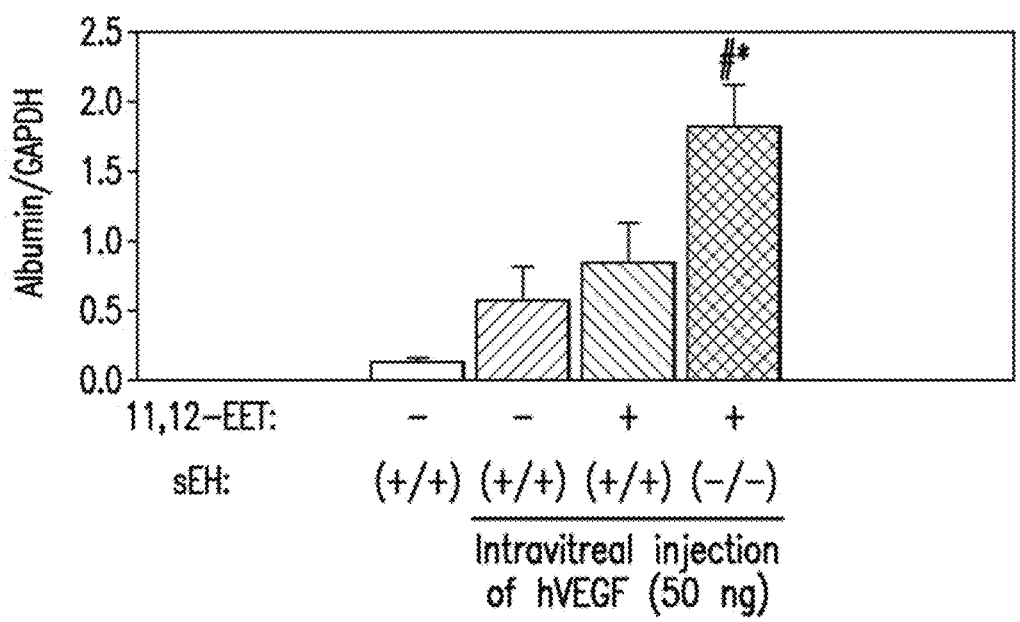
FIG. 8C is a bar graph of normalized relative density (albumin/GAPDH) from the autoradiograph of FIG. 8B.
Figure 9A:
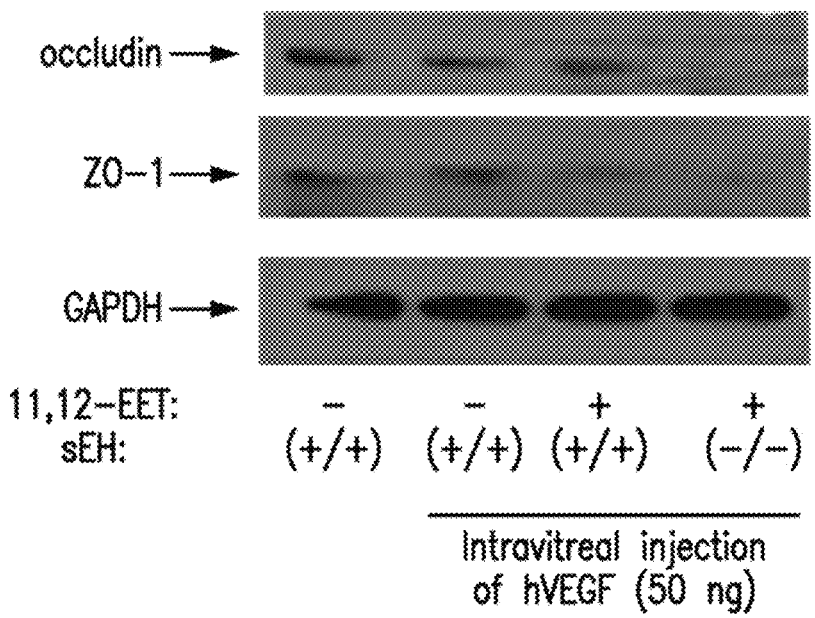
FIG. 9A is an autoradiograph of a Western blot for occludin, ZO-1, and GAPDH proteins in sEH (+/+) mice and sEH KO mice treated with or without 11,12-EET and intravitreal injection of recombinant human VEGF.
Figure 9B:
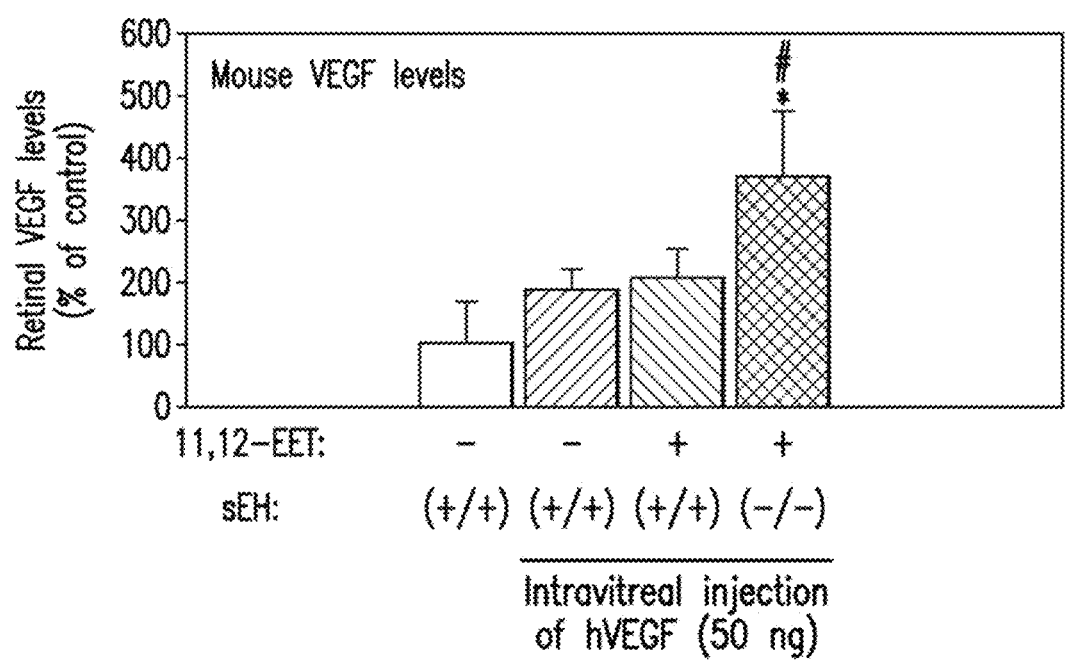
FIG. 9B is a bar graph of normalized relative density (albumin/GAPDH) from the autoradiograph of FIG. 9A.

Significant retinal albumin leakage was observed after intravitreal injection with recombinant human VEGF (hVEGF; R & D systems) in a dose-dependent manner (FIG. 8A). Notably, sEH KO potentiated the effects of 11,12-EET on intravitreal hVEGF-induced retinal vascular leakage (FIG. 8B), which is correlated with the reduction of retinal occludin and ZO-1 expression (FIG. 9A). Also, stabilization of 11,12-EETs by sEH KO augmented retinal VEGF levels (FIG. 9), which was consistent with the concept that EETs stimulate VEGF production. Interestingly, it has been shown that EET promotes VEGF expression via induction of STAT-3 binding to VEGF promoter. These results establish that rising EETs by sEH KO is a vital mechanism to enhance the effects of VEGF on retinal damage.

Example 10

11, 12-EET Promotes, Whereas EETs Blocker Attenuates, Intravitreal Ang II-Induced Retinal Albumin Leakage in Diabetes Methods and Materials One week after mice developed diabetes, diabetic and control mice were assigned to the following groups: Ang II (intravitreal injection with 5 µg/1 µL of Ang II); diabetes+ Ang II; diabetes+Ang II+11,12-EET (15 µg/kg/day, s.c.; Alzet); diabetes+Ang II+MS-PPOH (CAS No. 206052-02-0-(N-methylsulfonyl-6-(2-propargyloxyphenyl)hexanamide, a selective EETs blocker; 20 mg/kg/day, i.p); and control. 11,12-EET was used because it potentiates intravitreal Ang II-induced retinal damage (FIGS. 4A-4C); also, MS-PPOH was used in a previous study (Huang, H., Exp Biol Med (Maywood), 231:1744-1752 (2006)).

Results

Figure 10A:
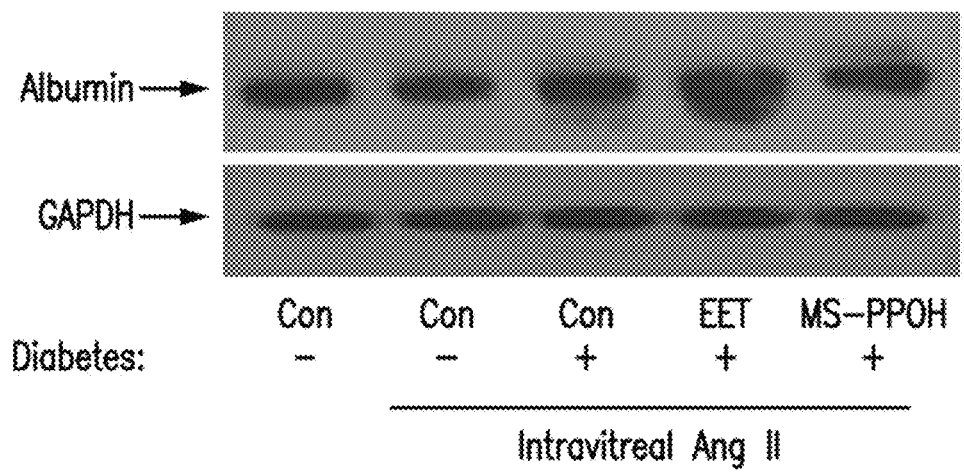
FIG. 10A is an autoradiograph of a Western blot for albumin and GAPDH in control mice and diabetic mice intravitreally treated with Ang II+EET or MS-PPOH.
Figure 10B:
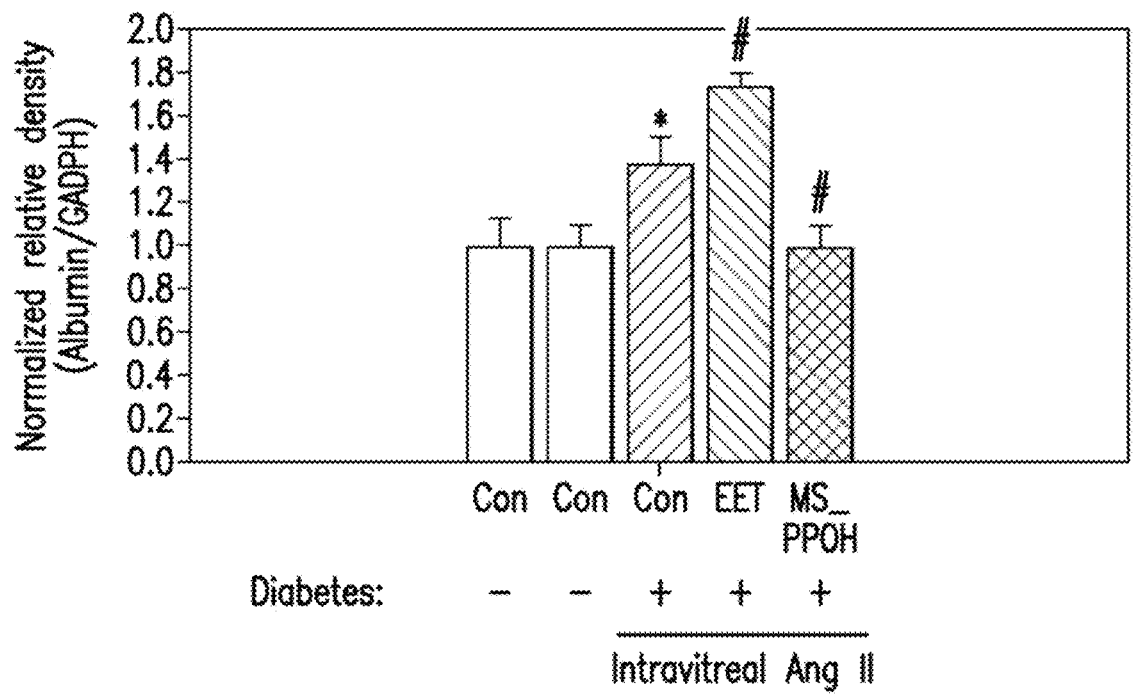
FIG. 10B is a bar graph of normalized relative density (Albumin/GAPDH) from the autoradiograph of FIG. 10A.

It was found that 1) local delivery of Ang II accelerates disruption of the blood retinal barrier and the occurrence of hyperpermeability in diabetes, as shown by significant increases in albumin leakage (FIGS. 10A and 10B); 2) 11,12-EET increased, whereas MS-PPOH decreased intravitreal Ang II-induced retinal albumin leakage in diabetic mice (FIGS. 10A and 10B); and 3) neither 11,12-EET (528±53 vs. 483±122 mg/dL) nor MS-PPOH (502±57 vs. 483±122 mg/dL) affected blood glucose levels in diabetic mice. These results suggest that circulating EETs or EETs blockade does not affect hyperglycemia or islet function after mice have developed diabetes. Taken together, these findings provide direct evidence that 11,12-EET potentiates, whereas EETs blockade attenuates, intravitreal Ang II-induced retinal damage in diabetes.

Example 11

Both 11, 12 EET and 14,15 EET Enhance GLUT-1 Expression in HREC Under HG and Hypoxia Methods and Materials HRECs were subjected to L-glucose (osmotic control), L-Glu+hypoxia (CoCl$_2$, 5 µM; CO), HG (25 mM of D-Glucose), or HG+CO.

Results

Figure 11A:
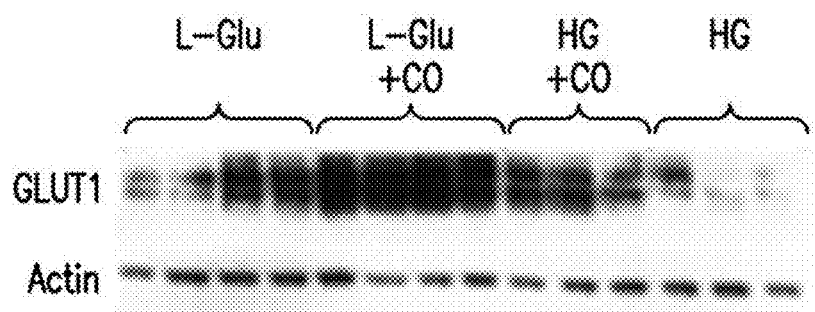
FIG. 11A is an autoradiograph of a Western blot of GLUT-1 expression under HG and hypoxia.
Figure 11B:
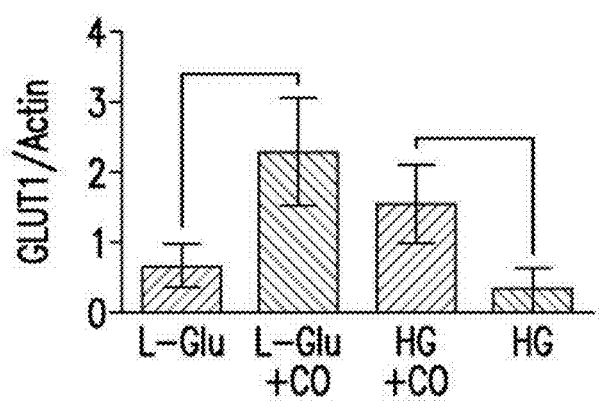
FIG. 11B is a bar graph of normalized density (GLUT/Actin) for the autoradiograph of FIG. 11A.
Figure 11C:
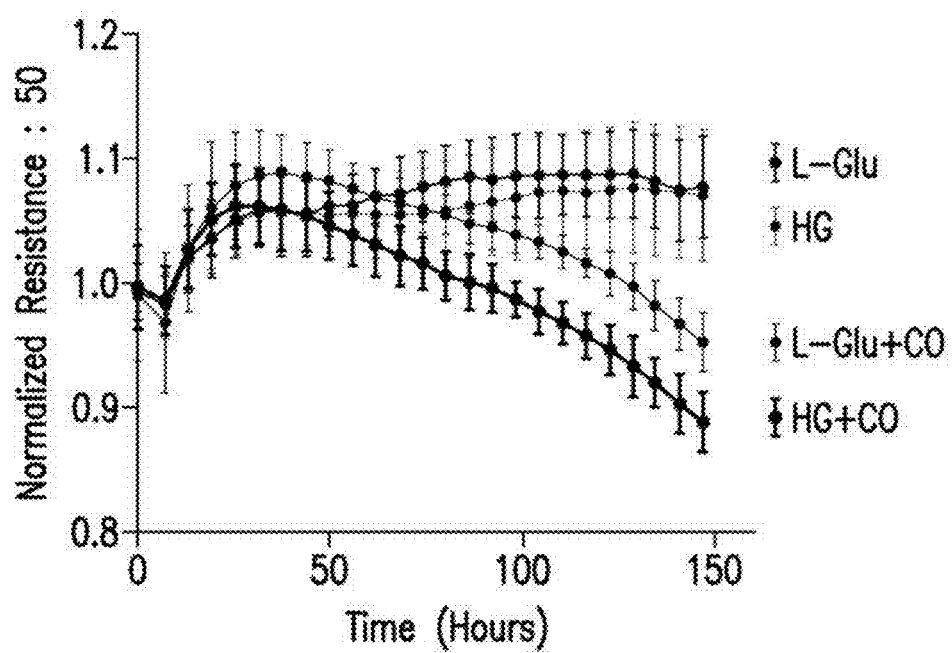
FIG. 11C is a line graph of normalized resistance by ECIS versus time (hours) in HRECs treated with L-Glu, HG, L-Glu+CO, and HG+CO.
Figure 11D:
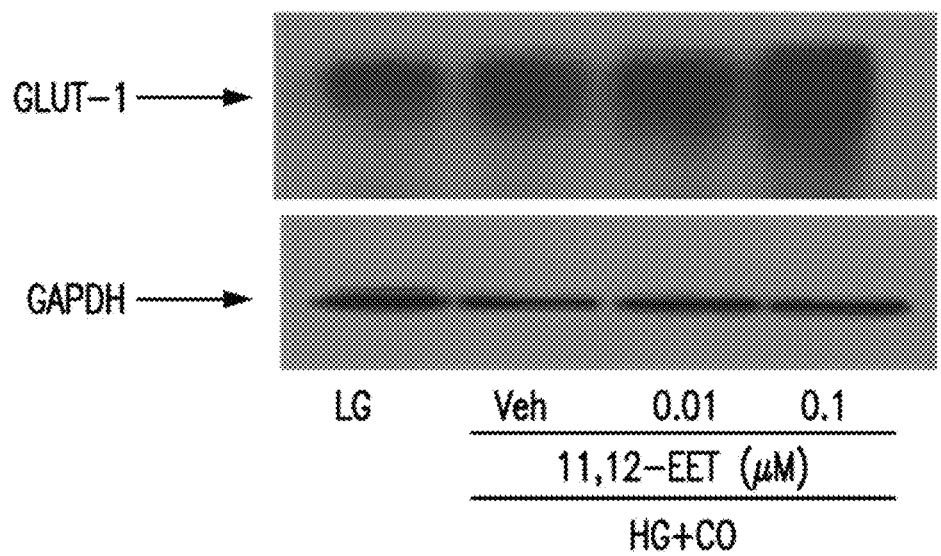
FIG. 11D is an autoradiograph of a Western blot of GLUT-1 expression in HRECs treated with 11,12 EET under HG+CO.
Figure 11E:
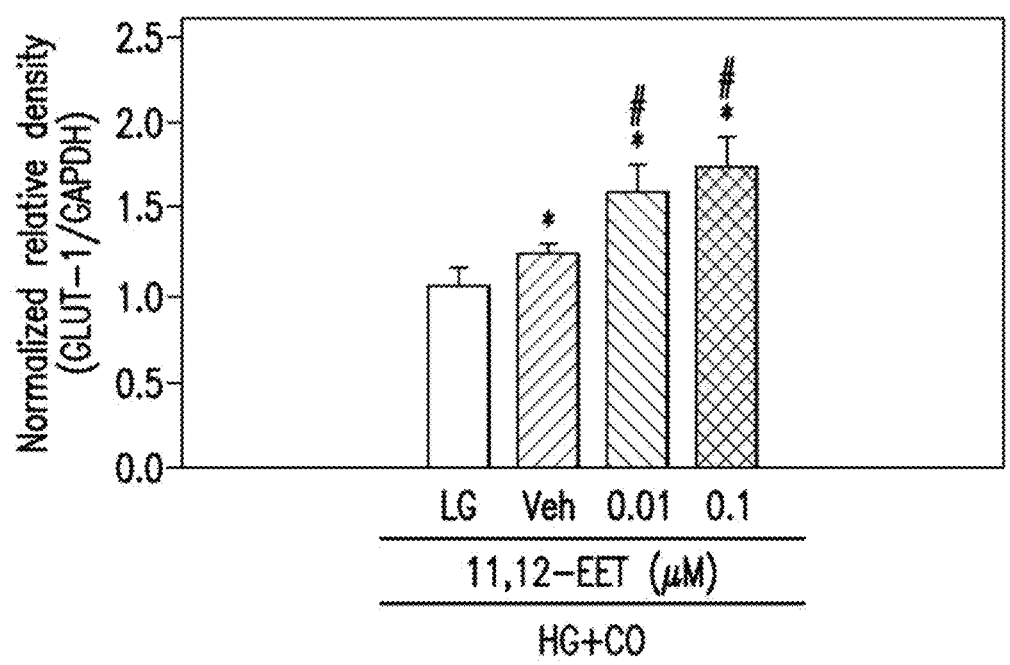
FIG. 11E is a bar graph of normalized relative density (GLUT-1/GAPDH) for the autoradiograph of FIG. 11D.
Figure 11F:
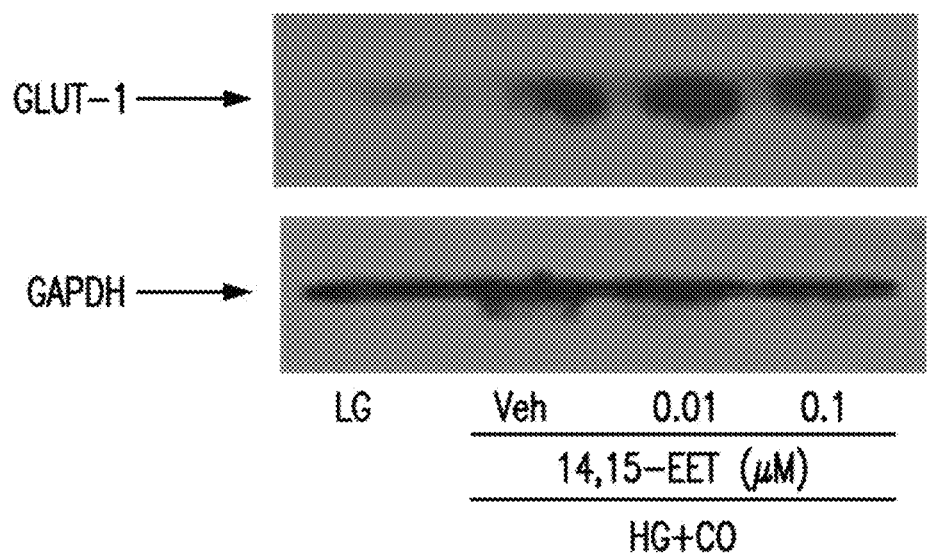
FIG. 11F is an autoradiograph of a Western blot of GLUT-1 expression in HRECs treated with 14,15 EET under HG+CO.
Figure 11G:
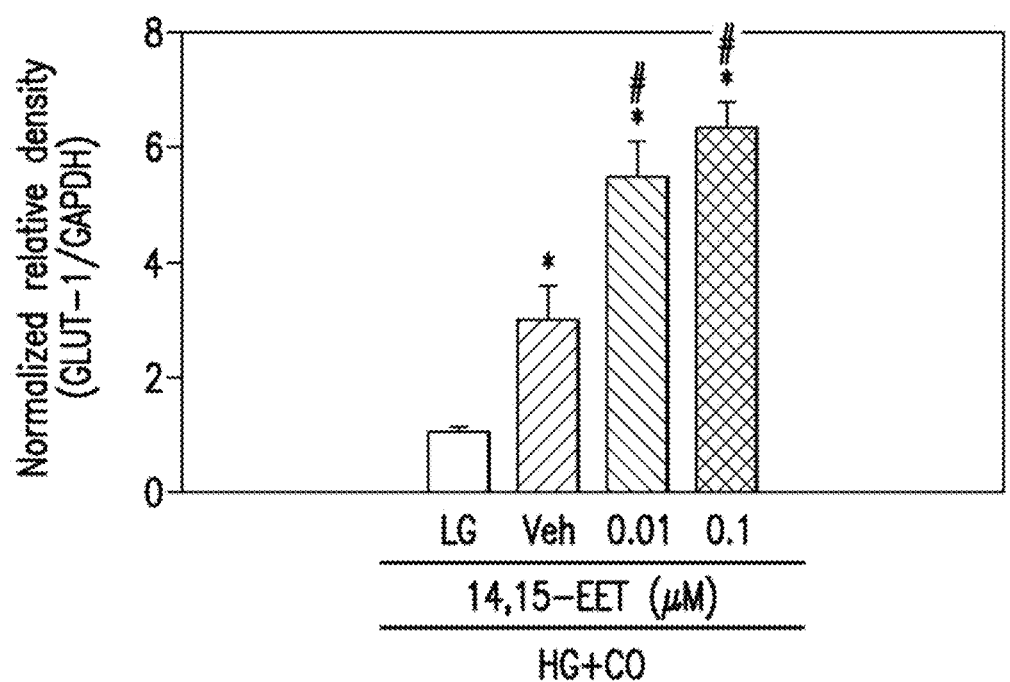
FIG. 11G is a line graph of normalized relative density (GLUT-1/GAPDH) for the autoradiograph of FIG. 11F.

HG alone decreased GLUT-1 expression, whereas hypoxia increased GLUT-1 expression under both L-Glu and HG conditions (FIGS. 11A and 11B). It was also found that HG alone does not change the barrier function unless HRECs were treated with hypoxia (FIG. 11B). Interestingly, both 11,12-EET (FIGS. 11C and 11D) and 14,15-EET (FIGS. 11E and 11F) promoted GLUT-1 expression in HRECs under HG CO, suggesting that EETs could act as endogenous lipid mediators to regulate glucose transport via GLUT-1 in HRECs under conditions of HG plus hypoxia.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for treating diabetic retinopathy in a subject in need thereof comprising:
    administering to the subject a pharmaceutical composition comprising:
    an EET antagonist is selected from the group consisting of N-methylsulfonyl-6-(2-propargyloxyphenyl)hexanamide [MS-PPOH]; 14,15-epoxyeicosa-5(Z)-enoic acid [14,15-EEZE]; 14,15-epoxyeicosa-5(Z)-enoic acid 2-[2-(3-hydroxy-propoxy)-ethoxy]-ethyl ester [14,15-EEZE-PEG]; 14,15-epoxyeicosa-5(Z)-enoic-methylsulfonylimide [14,15-EEZE-mSI]; and combinations thereof and a AT1 receptor antagonist selected from the group consisting of losartan, candesartan, eprosartan, irbesartan, olmesartan, telmisartan, valsartan and combinations thereof in an amount effective to treat the diabetic retinopathy.

2. A method for reducing progression of diabetic retinopathy in a subject in need thereof comprising:
    administering a pharmaceutical composition comprising:
    an EET antagonist is selected from the group consisting of N-methylsulfonyl-6-(2-propargyloxyphenyl)hexanamide [MS-PPOH]; 14,15-epoxyeicosa-5(Z)-enoic acid [14,15-EEZE]; 14,15-epoxyeicosa-5(Z)-enoic acid 2-[2-(3-hydroxy-propoxy)-ethoxy]-ethyl ester [14,15-EEZE-PEG]; 14,15-epoxyeicosa-5(Z)-enoic-methylsulfonylimide [14,15-EEZE-mSI]; and combinations thereof and a AT1 receptor antagonist selected from the group consisting of losartan, candesartan, eprosartan, irbesartan, olmesartan, telmisartan, valsartan and combinations thereof in an amount effective to reduce progression of diabetic retinopathy in the subject.

3. A method for treating a symptom of diabetic retinopathy in a subject in need thereof comprising:

administering a pharmaceutical composition comprising: an EET antagonist is selected from the group consisting of N-methylsulfonyl-6-(2-propargyloxyphenyl)hexanamide [MS-PPOH]; 14,15-epoxyeicosa-5(Z)-enoic acid [14,15-EEZE]; 14,15-epoxyeicosa-5(Z)-enoic acid 2-[2-(3-hydroxy-propoxy)-ethoxy]-ethyl ester [14,15-EEZE-PEG]; 14,15-epoxyeicosa-5(Z)-enoic-methyl-sulfonylimide [14,15-EEZE-mSI]; and combinations thereof and a AT1 receptor antagonist selected from the group consisting of losartan, candesartan, eprosartan, irbesartan, olmesartan, telmisartan, valsartan and combinations thereof in an amount effective to increase visual acuity in the subject.

\* \* \* \* \*